(12) United States Patent
Masse et al.

(10) Patent No.: US 8,486,688 B2
(45) Date of Patent: Jul. 16, 2013

(54) USE OF PSYCHROPHILIC ANAEROBIC DIGESTION IN SEQUENCING BATCH REACTOR FOR DEGRADATION OF PRIONS

(75) Inventors: Daniel Y. Masse, Sherbrooke (CA); Yun Xia, Lennoxville (CA)

(73) Assignee: Bio-Terre Systems Inc. (CA)

( * ) Notice: Subject to any disclaimer, the term of this patent is extended or adjusted under 35 U.S.C. 154(b) by 214 days.

(21) Appl. No.: 12/817,532

(22) Filed: Jun. 17, 2010

(65) Prior Publication Data

US 2011/0312099 A1 Dec. 22, 2011

(51) Int. Cl.
*C02F 3/28* (2006.01)
*G01N 33/68* (2006.01)
*C07K 14/78* (2006.01)

(52) U.S. Cl.
USPC .......... 435/262.5; 435/267; 435/262; 436/86; 530/356; 530/357; 530/353

(58) Field of Classification Search
None
See application file for complete search history.

(56) References Cited

U.S. PATENT DOCUMENTS

| | | | | |
|---|---|---|---|---|
| 5,863,434 A * | 1/1999 | Masse et al. | ................. | 210/603 |
| 7,416,644 B2 * | 8/2008 | Bonde | ............................ | 203/14 |
| 2010/0297740 A1 * | 11/2010 | Li et al. | ......................... | 435/267 |

FOREIGN PATENT DOCUMENTS

| CA | 2138091 | 6/1996 |
|---|---|---|
| WO | WO2010/132987 | 11/2010 |

OTHER PUBLICATIONS

Kirchmayr, R. et al. Prion protein: detection in "spiked" anaerobic sludge and degradation expreriments under anaerobic conditions. Water Sci. Technol. 2006. vol. 53, No. 8, pp. 91-98, ISSN:0273-1223; the whole document especially p. 93.
Hinckley, G.T. et al. Persistence of Pathogenic Prion Protein during Simulated Wastewater Treatment Processes. Environ. Sci. Technol. 2008. vol. 41, pp. 5254-5259, ISSN:0013-936X; the whole document.
Masse, D.I. et al. Psychrophilic anaerobic digestion biotechnology for swine mortality disposal. Bioresource Technology. 2008. vol. 99, pp. 7307-7311, ISSN:0960-8524.
Cote, C. et al. Reduction of indicator and pathogenic microorganisms by psychrophilic anaerobic digestion in swine slurries. Bioresource Technology. 2006. vol. 97, pp. 686-691, ISSN: 0960-8524.
Okoroma, E.A. et al. 'Keratinase production by proteolytic microorganisms in activated sludge and farmyard waste' In: Society for General Microbiology, 163rd Meeting, Dublin, Ireland. Sep. 8-11, 2008. Posters Fermentation and Bioprocessing Group, p. 53, FB02.
Okoroma, E.A. et al. 'Bacterial Keratinase: Prospects for Prion Degradation'. In: Society for General Microbiology, 164th Meeting. Harrobate. Mar. 30-Apr. 2, 2009. Posters Prions, p. 53, HAR21/02.
International Search Report of corresponding International application No. PCT/CA2010/000953 dated Mar. 10, 2011.

* cited by examiner

*Primary Examiner* — Yelena G Gakh
*Assistant Examiner* — Michelle Adams
(74) *Attorney, Agent, or Firm* — Cantor Colburn LLP

(57) ABSTRACT

The use or process of use of a sequencing batch reactor for eliminating prion in specified risk materials and for measuring the efficacy of a sequencing batch reactor to degrade prior proteins in specified risk materials are disclosed. The specified risk material is fed to a sequencing batch reactor containing a layer of acclimatized anaerobic sludge, and the specified risk material reacts with the sludge at a temperature below 25° C. so as to allow degradation of the prion protein.

5 Claims, 19 Drawing Sheets

USE OF PSYCHROPHILIC ANAEROBIC DIGESTION IN SEQUENCING BATCH REACTOR FOR DEGRADATION OF PRIONS

TECHNICAL FIELD

The present invention relates to the use or process of use of a sequencing batch reactor for eliminating prion in specified risk materials.

BACKGROUND ART

Prions are proteins devoid of nucleic acids and cell membranes which are largely unaffected by standard methods of sterilisation. Prions are unprecedented infectious pathogens that cause a group of invariably fatal neurodegenerative diseases by an entirely novel mechanism (Prusiner, 1998, Proc Natl Aca Sci, 95: 13363-13383). Inactivation of prions poses significant environmental and health issues both for the disposal of prions infected animals and in the preparation of materials of animal origin, such as animal feed. Slaughterhouse sludge and animal mortalities (carcasses) are an important source of pathogens or infectious prions proteins.

Prions are protein naturally found in animals. Cellular or normal form of prion proteins are constitutively expressed in the brains of healthy adult animals, but are highly regulated, both spatially and temporally, during development (Prusiner, 1998, Proc Natl Aca Sci, 95: 13363-13383). There are two isoforms of prion proteins. PrPC (Prion Protein Cellular isoform) is a cell surface, N-linked, α-helices-rich, globular soluble glycoprotein protein that may serve as a signal transduction protein (Mouillet-Richard et al., 2000, Science, 289: 1925-1928) and may play an essential role in the normal development of mammal brain. PrPC occurs both in healthy and diseased tissues. PrPSc (Prion Protein Scrapie agent) is a β-sheet-rich, fibrous, highly insoluble protein which is the causative agent of central nervous system diseases in mammals. It is thought that a higher content in β-sheet confer heat- and protease-resistance to PrPSc.

The presence of the abnormal, pathological isoform (PrPSc) is typical of the diseased state. PrPC and PrPSc are identical in their primary structure. Differences occur in secondary structures: PrPC contains three α-helices (about 40% α-helix) and a short antiparallel β-sheet, whereas PrPSc is composed of two α-helices (about 30% α-helix) and four β-sheets (45% β-sheets) (Prusiner, 1998, Proc Natl Aca Sci, 95: 13363-13383)). This induces conformational changes in the tertiary structure of PrPSc, resulting in modified characteristics. Both PrP isoforms are devoid of nucleic acids (Prusiner, 1998, Proc Natl Aca Sci, 95: 13363-13383).

Experimental data suggests that prions can survive for a long time in natural environments. For example, Brown and Gajdusek (1991, J Infect Dis, 153: 1145-1148) showed that prions buried into a garden soil could survive and retain their infectivity power for 3 years, with little leaching deeper into the soil.

Current research suggests that the primary method of infection in animals is through ingestion. It is thought that prions may be deposited in the environment through the remains of dead animals and via urine, saliva, and other body fluids. They may then linger in the soil by binding to clay and other minerals. Sterilizing prions involves the denaturation of the protein to a state where the molecule is no longer able to induce the abnormal folding of normal proteins. However, prions are generally quite resistant to proteases, heat, radiation, and formalin treatments, although their infectivity can be reduced by such treatments. Effective prion decontamination relies upon protein hydrolysis or reduction and/or destruction of protein tertiary structure. Examples include bleach, caustic soda, or strong acidic detergents.

Transmissible Degenerative Encephalopathies. (TDE) forms a group of fatal neurodegenerative disorders caused by the accumulation of prions in the brains of mammals. TDE are unique in that the host's normal prion protein (PrPc) is modified into the infective prion protein (PrPsc) as a consequence of infection (Carp et al., 1985, J Gen Virol, 66: 1357-1368), and forms deposits in affected tissues, especially in the central nervous system. TDE affect a wide variety of wild animals and livestock, as well as humans, and present in 3 ways, all of which involve modifications of the prion protein: heritably as a result of genetic mutations; sporadically by spontaneous conversion of the prion protein into a pathologic form via yet undefined mechanisms; by infection following exposure to the exogenous misfolded form of the prion protein.

Bovine Spongiform Encephalopathy (BSE) is among the most notable prion disease. The International Trade Commission (ITC) released a report estimating that trade restrictions resulting from Bovine BSE cost the cattle industry $11 billion from 2004 to 2007.

Thus, not only are animal manure management practices are often detrimental to the environment, they also represent a potential hazard to human and animal health, in addition in producing strong odours, encourage fly breeding, induce weed problems and pollute air, soil and water.

The Canadian Food Inspection Agency estimated the amount of specified risk materials (SRM) generated in Canada at 170,000 tonnes annually. Safe disposal of SRM potentially contaminated with prions is challenging since these TDE-causing agents are relatively resistant to inactivation by physical or chemical procedures usually applied for microorganisms (Taylor et al., 1994, Arch Virol, 139: 313-326). Moreover, significant costs are associated with some disposal treatment. Physical and chemical methods of prions inactivation that efficiently and/or rapidly fix proteins, including alcohols, aldehydes and rapid heating with steam, protect prions from inactivation, hence enhancing their thermo stability. Thus, treatments that disrupt protein structure, rather than fixing it, are required when considering the disposal of SRM potentially contaminated with prions. Moreover, treatments using chemicals such as denaturants, detergents, strong alkali are inappropriate for the inactivation of prions in SRM due to potential user exposure at the farm and disposal problems onto agricultural land.

Consequently, there is a need to develop biological treatments for the degradation of prions in SRM which are environmentally sound.

It would be thus highly desirable to be provided with a process that eliminates prion protein in specified risk materials from animal that is low in cost, is very stable, simple, easy to operate and which does not interfere with regular farm operations.

SUMMARY

In accordance with the present disclosure there is now provided a process for degrading a prion protein in a specified risk material comprising the steps of feeding the specified risk material (SRM) to a sequencing batch reactor (SBR) containing a layer of acclimatized anaerobic sludge; and allowing the specified risk material to react with the sludge at a temperature below 25° C. so as to allow degradation of the prion protein.

It is also provided a process of measuring the efficacy of a sequencing batch reactor (SBR) to degrade prion proteins in a specified risk material comprising the steps of feeding the specified risk material (SRM) to the sequencing batch reactor (SBR) containing a layer of acclimatized anaerobic sludge; adding a model protein to the SBR; and allowing the specified risk materials and model protein to react with the sludge at a temperature between 5° C. to 25° C., wherein degradation of the model protein is indicative of the efficiency of the SBR to degrade prion proteins in the SRM.

In a preferred embodiment, the specified risk material comprises animal carcasses.

In another embodiment, the anaerobic sludge is derived from swine manure, dairy manure and/or slaughterhouse sludge.

In a preferred embodiment, the specified risk material reacts with the sludge at a temperature between 5° C. to 25° C.; preferably at a temperature between 20° C. to 25° C.; more preferably at a temperature of 20° C.

In another embodiment, the process of degrading a prion protein in a specified risk material as described herein also comprises the step of adding keratin to the SBR. The keratin can be from feather keratin or hoof keratin, and correspond to β-keratin or α-keratin. Preferably, the feather keratin is from chicken feather and the hoof keratin is from bovine hoof.

In another embodiment, the SBR is an anaerobic digestion sequencing batch reactor or a mesophilic anaerobic digestion sequencing batch reactor.

In another embodiment, the model protein described herein can be at least one of perchloric acid-soluble protein, collagen, elastin and keratin.

A "specified risk material" is intended to mean any material that may contain prions concentrate therein, such as tissues of ruminant animals. Such material can include the brain, skull, eyes, trigeminal ganglia, spinal cord, vertebral column, dorsal root ganglia, and the tonsils and distal ileum of the small intestine for example.

BRIEF DESCRIPTION OF THE DRAWINGS

Reference will now be made to the accompanying drawings.

DETAILED DESCRIPTION

Figure 1:
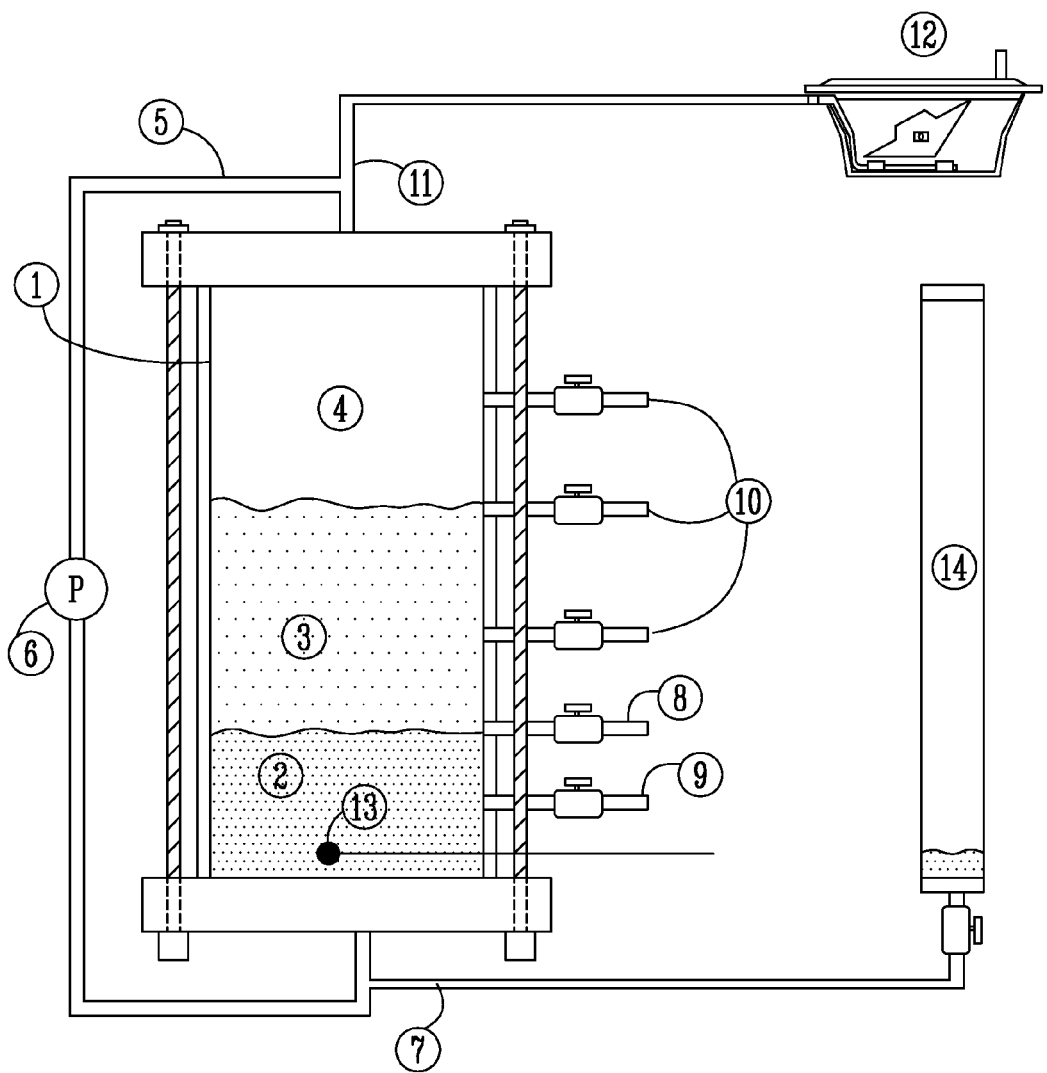
FIG. 1 illustrates a schematic representation of a laboratory scale sequencing batch reactor.
Figure 2A:
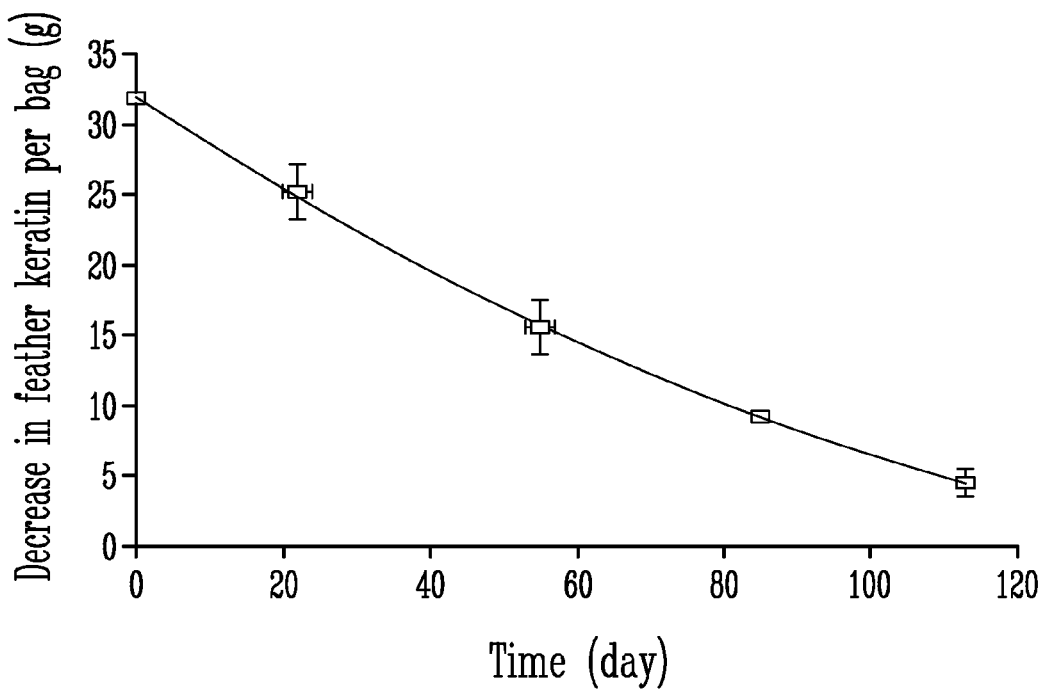
FIGS. 2A and B illustrate a graphic representation of feather keratin decrease in bags in reactors supplied with feather keratin.
Figure 2B:
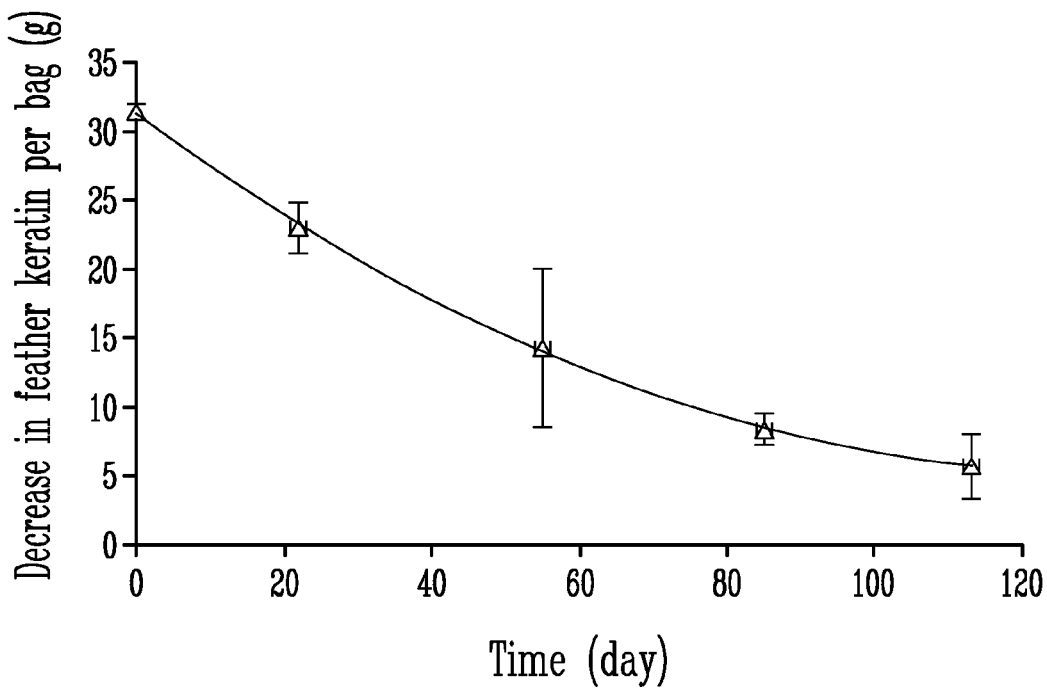

It is provided the use of psychrophilic anaerobic digestion sequencing batch reactor (PADSBR) and mesophilic anaerobic digestion sequencing batch reactor (MADSBR) technologies for eliminating prion in specified risk materials (SRM), reducing the risk of biological contamination of fauna, soil, groundwater and surface water.

Incineration is currently the primary method by which SRM are disposed in Europe. Laboratory results suggested that prions in SRM are unlikely to survive incineration (Taylor et al., 1996, Neuropath Appl Neuro, 22: 256-258). However, this treatment is expensive and precludes any value to be derived from the SRM. Furthermore, incineration is impractical in many regions due to the geographical dispersal of the cattle populations, which involves supplementary costs and unacceptable contamination risks associated to the transportation of prion-contaminated SRM.

Exceptional resistance of prions to dry heat has been observed in lyophilized samples or in samples dried onto glass or steel surfaces. Primary study revealed that gravity-displacement autoclaving at 134° C. for 1 h eliminates prions. However, paradoxical results were provided by studies achieved with porous-load autoclaving: data suggested that the thermostability of prions was enhanced as the temperature of autoclaving was increased (134 to 138° C.) (Taylor, 1999, Vet Microbiol, 67: 13-16). This indicates that increasing the temperature or exposure time of prion-infected SRM to porous-load autoclaving would not be effective for reliable decontamination.

Ionizing, ultraviolet and microwave irradiations have little effect on prions (Taylor and Diprose, 1996, Neuropath Appl Neuro, 22: 256-258). It is generally acknowledged that the inactivating effect of microwaves on microorganisms is due to the heat generated.

Strong sodium hypochlorite solutions or hot solutions of sodium hydroxide seem to be the only methods that completely inactivate prions, whereas concentrated formic acid substantially reduces the infectivity level in histologically-fixed tissue. Prions are not completely inactivated by exposure to autoclaving or sodium hydroxide solutions, but combining these two treatments can achieve inactivation. However, chemical treatments for inactivating prions are impractical for full-scale, on-farm disposal strategies of bovine slaughterhouse sludge or carcasses since the chemicals added to SRM may negatively affect their fertilizer value.

Concentrated formic acid solubilises proteins. As is the case for irradiations, there is little effect on prions after exposure to ethylene oxide, glutaraldehyde, formalin, β-propiolactone or acetylethyleneimine.

The only detergent that has some effect on prions is sodium dodecyl sulfate (SDS), but reports showed that SDS must be used only for contaminated fluids (Taylor et al., 1999, Vet Microbiol, 67: 13-16). Therefore, treating SRM with SDS or other detergents seems impractical.

Organic solvents including ethanol, ether, acetone, 5% chloroform, 4% phenol, proprietary phenolic disinfectants and commercial solvent-extraction processes involving hexane, heptane, perchloroethylene or petroleum are weakly effective for reducing prions infectivity.

Scrapie agents exposed to 3% hydrogen peroxide, chlorine dioxide, or peracetic acid were not or only slightly inactivated.

All these known treatment are associated with significant costs; in some cases protect prions from inactivation, hence enhancing their thermostability; disrupt protein structure, rather than fixing it; and are inappropriate for the inactivation of prions in SRM due to potential user exposure at the farm and disposal problems onto agricultural land.

Consequently, biological treatments for the degradation of prions in SRM which are environmentally sound represent an alternative as described herein.

Anaerobic digestion of organic matter is a process used for treatment of organic waste and production of energy. In anaerobic bioreactors, organic matter is removed from the wastewater by the concerted action of various groups of microorganisms. The activity of the microbial species participating in mineralization of organic matter is of crucial importance for obtaining an efficient degradation of organic material in bioreactors. During anaerobic digestion, the organic matter is converted via acetate, short chained volatile fatty acids (like propionate, butyrate and iso-butyrate) and hydrogen/carbon dioxide to methane by the activity of a complex microbial consortium consisting of hydrolytic/fermentative acidogenic bacteria, acid-oxidizing bacteria and methanogenic archaea. Four major groups of microorganisms have been identified with different functions in the overall degradation process. The first group represent the hydrolyzing and fermenting microorganisms which are responsible for the initial attack on polymers and monomers found in the waste material and produce mainly acetate and hydrogen, but also varying amounts of volatile fatty acids (VFA) such as propionate and butyrate as well as some alcohols; group 2 represent the hydrogen-producing acetogenic bacteria which convert propionate and butyrate into acetate and hydrogen; two groups (3 and 4) of methanogenic Archaea produce methane from acetate or hydrogen, respectively.

Bovine slaughterhouse sludge and carcasses are substrates composed of readily biodegradable organic matter that can be converted into a high quality biogas which can be processed into thermal and electrical energy. Slaughterhouse wastes are well suited to anaerobic treatment and high solids removal is achieved. The effluent concentrations in heavy metal (cadmium, cobalt, nickel, copper, chromium) are below detectable limit. Nutrients such as calcium, magnesium, sulphur and iron are in concentration adequate for biological treatment of the wastewater. Slaughterhouse effluents are generally coagulated and flocculated to remove colloidal material and suspended solids responsible for the color and turbidity (Al-Mutairi, 2006, Ecotoxicology and Environmental Safety, 65: 74-83). Floc-forming compounds such as lime, alum, sodium aluminates, ferric chloride and ferrous sulphate are used to remove suspended solids.

The sludge produced are mainly composed of blood, paunch, stomach contents, undigested food, urine, loose meat, soluble proteins, fat, fecal matters, etc. The proportions of these elements in the sludge vary between slaughterhouses. Al-Mutairi (2006, Ecotoxicology and Environmental Safety, 65: 74-83) indicated that alum and polymer used to coagulate and flocculate solids from slaughterhouse effluents can be toxic to the microflora of a subsequent biological treatment process. When the concentrations of a coagulant exceed 100 mg/l in the sedimentation tank, the effluent is toxic to microorganisms. Settled sludges are more contaminated and toxic than the sedimentation tank supernatant.

Hygienic aspects are important when an external feedstock is brought on a livestock farm for co-digestion. Effluent from poultry and swine abattoir can be contaminated with biological contaminants. Pathogens removal prior to land application is important to prevent reintroduction of contamination cycles in livestock production systems.

The fate of prions in anaerobic biological treatment has been reported only once (Kirchmayr et al., 2006, Wat Sci Technol, 53: 91-98). No reduction of prion titer was observed in mesophilic conditions (Kirchmayr et al., 2006, Wat Sci Technol, 53: 91-98).

FIG. 1 is a schematic illustration of a laboratory scale sequencing batch reactor (SBR) as used in the present disclosure and as described in Canadian patent No. 2,138,091, the content of which is enclosed herewith by reference. Each of the reference numerals refer to the following:

1. bioreactor;
2. sludge bed zone;
3. fill zone;
4. gas space;
5. biogas recirculation line;
6. biogas recirculation pump;
7. feeding line;
8. emptying port;
9. sludge sample port;
10. mixed liquor or supernatant sampling port;
11. gas outlet;
12. gas meter;
13. thermocouple; and
14. feeding system.

In the SBR shown in FIG. 1, the manure is loaded into the feeding system 14 and fed to the bioreactor 1 through the feeding line 7. The manure is fed through the bottom of the bioreactor 1 which has been pre-inoculated with an anaerobic sludge 2. The biogas in the bioreactor 1 can be recirculated in the gas spaced 4 through the biogas recirculation line 5 using the biogas recirculation pump 6.

It is thus described herein the use of SBR for decontaminating animal brain, eliminating prions and reducing the risks of biological contamination of soil, groundwater and surface water.

Experiments performed with the infectious isoform of prion proteins (PrPSc) require a biosafety level 3 laboratory. Proteins that resembles PrPSc in their structure (number of amino acids, high proportion of glycine residues, high content of β-sheet structures, high degree of aggregation) and properties (protease- and heat-resistance, weak solubility)

have been selected to confirm the efficacy of SBR to degrade prion proteins in swine manure or dairy manure (Arai et al., 1996, J Appl Polym Sci, 60: 169-179; Caughey and Raymond, 1991, J Biol Chem, 266: 18217-18223; Pan et al., 1993, Proc Natl Acad Sci USA, 90: 10962-10966; Prusiner et al., 1998, Cell, 93: 337-348; Weissmann, 1999, J Biol Chem, 274: 3-6). Non-limiting examples of such suitable model proteins to be added to an anaerobic digestion sequencing batch reactor (AD-SRB), in order to mimic and study the fate of prions in these bioreactors, are disclosed hereinbelow.

Perchloric acid-soluble protein (PSP) has been isolated (14.149 kDa protein with 137 amino acid residues) from rat kidney, brain and lung, as well as from rat, pig and chick livers (Hui et al., 2004, Biochem Biophys Res Commun, 321: 45-50). The secondary structure of that protein (2α-helices and 6β-sheets) resembles that of PrPSc (2α-helices and 4β-sheets). PSP is heat-stable and proteinase K resistant, as is PrPSc. This suggests that PSP would be a suitable model protein for studying the fate of PrPSc in the AD-SBR.

Collagen is the most abundant protein in mammals, representing 25% of total proteins. Collagen is a major, fibrous, insoluble, extracellular protein of skin, tendon, cartilage, bone and teeth, and serves to hold cells together.

Elastin is a fibrous cross-linked protein in the extracellular matrix that provides elasticity for many tissues which can stretch to several times their length and return to their original state when the tension is released. Elastin is found in large amounts in the walls of blood vessels and in ligaments, particularly in the neck of grazing animals.

Keratins forms one of the most diverse classes of fibrous proteins. There are various types of keratins, each composed of a complex mixture of proteins. Keratins are major constituents of structures that grow from the skin. α-Keratins are found in the hair (including wool), horns, nails, claws and hooves of mammals. A hoof is the tip of a toe of an ungulate mammal, strengthened by a thick horny (keratin) covering. The hoof consists of a hard or rubbery sole, and a hard wall formed by a thick nail rolled around the tip of the toe.

α-Keratins are the most prevalent forms and are composed largely of polypeptide chains in the α-helix conformation. The harder β-keratins are alternative forms that exist in the claws, scales and shells of reptiles, and in the claws, scales, beaks and feathers of birds (Zubay, 1988, Biochemistry, New York, N.Y., USA: Macmillan Publishing Company). β-Keratins are composed of stacked and folded β-sheets, and better represent PrPSc. The amino acid sequences of β-keratins from various bird species are highly similar and, like collagen and elastin, contain a high proportion of glycine (Harrap and Woods, 1964, Biochem J, 92: 19-26). Glycine-rich repeats are found in some, but not all, β-keratins. β-keratins are shorter (98 to 155 amino acids) than PrP proteins (256 to 264 amino acids).

α-Keratins are composed of extremely long α-helical polypeptide chains that are arranged side by side to form fibers in a spiral fashion. The packing of α-helices is optimized and strengthened by wrapping of individual helices around each other. Many forms of α-keratins include (covalent) disulfide bonds formed between cysteine residues of adjacent polypeptide chains, which confers permanent, thermally-stable cross linking. The amount of disulfide bridges modulates strength and rigidity in keratins. Approximately one quarter to one third of feather keratins have a β-conformation, mostly concentrated in the central, hydrophobic portion of the molecule. The rest of the protein forms an irregular matrix. Closely related β-keratins are the main constituent of bird feathers and account for about 90% of the feather rachis.

Slaughterhouse inoculums was used-herein, collected from a semi-industrial scale anaerobic sequence bench bioreactor (AD-SBR). The SBR reactor is running at 20° C. and fed every week with fresh sludge from a commercial cattle slaughterhouse (Colbex, Levinoff, Québec) that processes about 1000 cattle per day. Every week about 50 kg of slaughterhouse sludge was collected and a representative sub-sample (1 L) was stored at 20° C. for later analysis and what was left was used to feed the semi-industrial SBR reactor.

The swine manure inoculums also used herein was collected from a semi industrial scale anaerobic sequence bench bioreactor (AD-SBR). Similarly, it is kept at 20° C. and fed every week with fresh sludge from a commercial pig farm (1944 ch. Tremblay. Ste-Edwidge, Québec) that processes about 4000 pigs per year. Every week about 50 kg swine manure was collected and a representative sub-sample (1 L) was stored at 20° C. for later analysis and what was left was used to feed the semi-industrial SBR.

It is also described the use of acclimatized anaerobic sludge as starting material. When there is an important change in the bioreactor's feed composition, the bacterial sludge needs time to adapt to the new substrate. Sometime, the new substrate in the feed can inhibit the sludge microflora. Usually, the performance of the bacterial increases with time. The anaerobic sludge is acclimatized when the sludge reaches the highest specific methane production (liter of methane per gram of feed) and when this maximal performance is maintained with time.

Feather is one of the large solid wastes in North America. Feathers are mainly composed of keratins. Keratins are insoluble and show high mechanical stability and resistance to proteolysis. Feather keratins are a β-keratin composed of mainly stacked and folded β-sheets; therefore, feather keratins are poorly digested by common digestive enzymes, such as trypsin and pepsin because of the high degree of cross-linking by disulphide bonds, hydrogen bonding and hydrophobic interactions (Papadopoulos, 1986, Animal Feed Science and Technology, 14: 279-290). A similar structure is found in pathagenous protein (PrPsc). Therefore, chicken feathers are used as model proteins of PrPsc due to feather keratins having a number of amino acids, high proportion of glycine residues, high content of β-sheet structures, high degree of aggregation and properties (protease and heat resistance, weak solubility) similar to prion proteins.

Similarly, hooves are also used as model proteins of PrPsc due to their high contant in hard keratins, insoluble and resistant to degradation by common proteolytic enzymes, such as trypsin, pepsin and papain because of their high degree of cross-linking by disulfide bonds, hydrogen bonding and hydrophobic interaction.

Degradation of feather keratin in AD-SBRs is demonstrated herein (see Table 1 for exemplified conditions). Decrease in feather keratin in bags was found in reactors as shown in FIG. 2A and FIG. 2B. Feather keratin in each reactor almost decreases linearly from 31 g at the beginning of the SBR run to 5 g within 120 days. On the contrary, no or very little decrease in feather keratin was found in bags in reactors fed with water containing antibiotics. Addition of feather keratin affected the gas production in reactors. As shown in FIG. 3A, gas production in all reactors with and without feather keratin increased exponentially in the first 15 days. After 15 days, gas production in control reactors gradually increased to the end of the experiment. No gas production was observed for a certain period. After the lag, gas production started again in reactors at a higher rate than in the control reactors. In average, gas produced in reactors with feather keratin is 1.2 times higher than that produced in control reactors without feather keratin. Addition of feather keratin stimulated gas production.

Figure 3A:
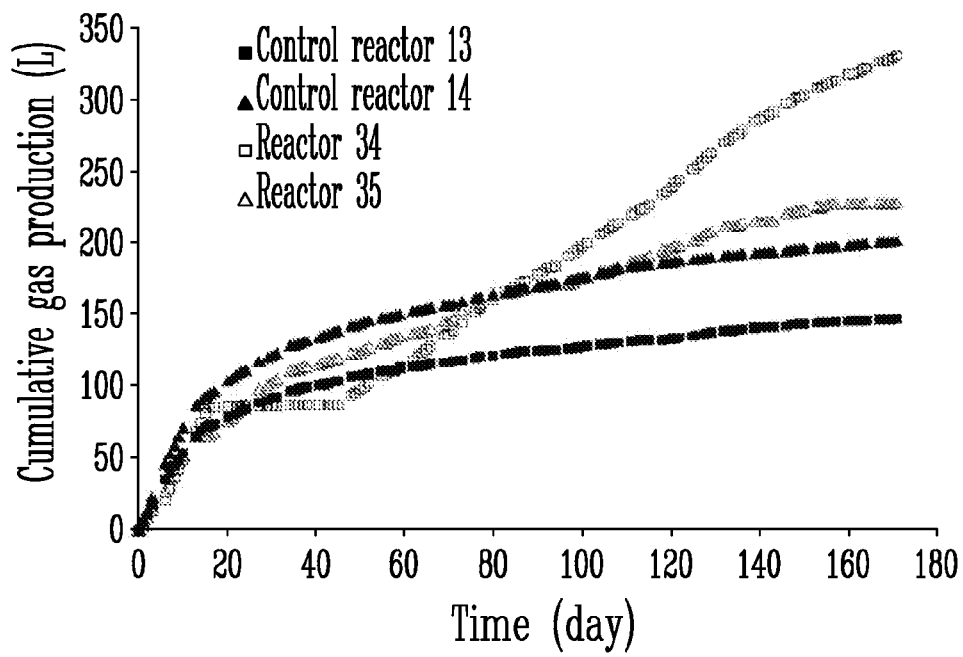
FIG. 3 illustrates the gas production measured in reactors, and more specifically in (A) the cumulative gas production and in (B) the daily gas production in reactors with (reactors 34 and 35) and without feather keratin (reactors 13 and 14).
Figure 3B:
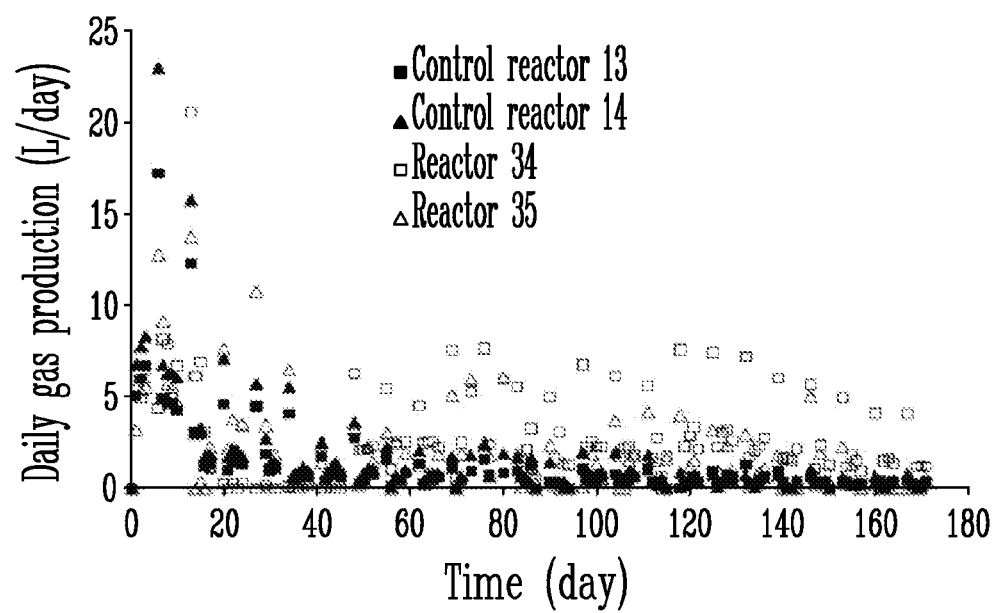

The effect of feather keratin on gas productions could also be seen on daily gas production rates. As shown in FIG. 3B, production rates in all reactors fluctuate within 3-23 L/day in the first 13 days. After that, gas production rates in control reactors gradually decreased to less than 1 L/day at the end of the experiment. However, gas production rates in reactors with feather keratin still fluctuated from 0 to 7.7 L/day after 13 days and remain the same trend to the end of experiment. The average rate measured in reactors is 1.6 times higher than that observed in control reactors.

Figure 4A:
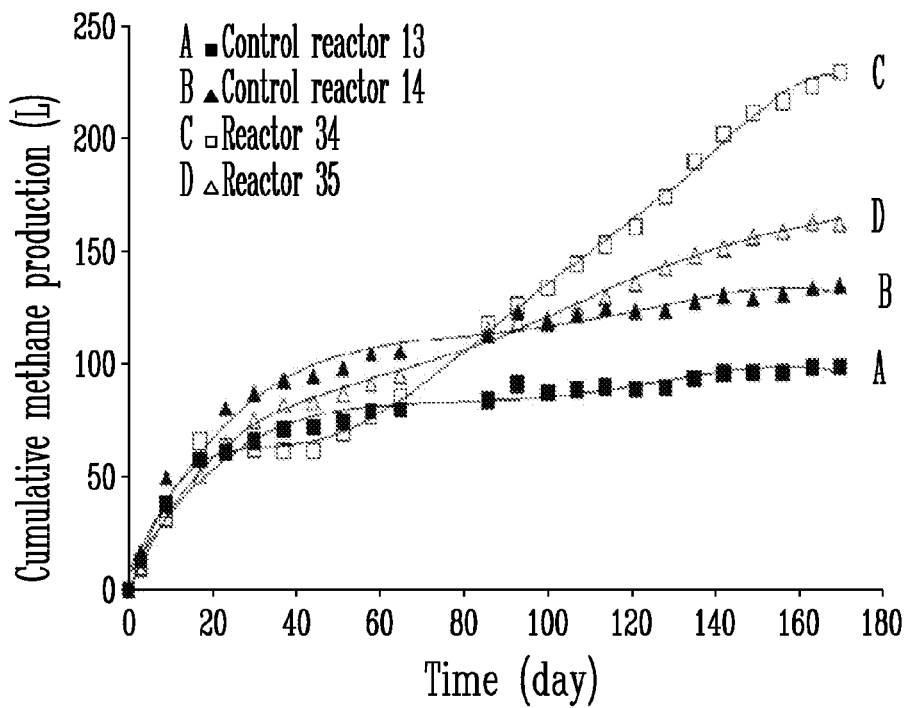
FIG. 4 illustrates in (A) the cumulative methane production, (B) acetic acid concentrations, (C) propionic acid concentrations and (D) propionic acid profiles measured in reactors with (reactors 34 and 35) and without feather keratin (reactors 13 and 14).
Figure 4B:
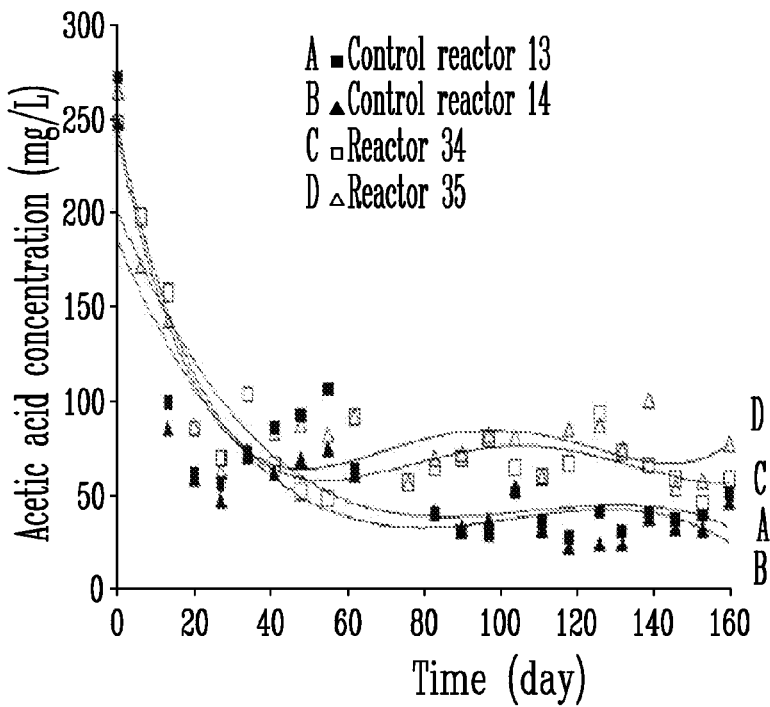

Effect of feather keratin addition on gas production could also be seen on the cumulative methane production profiles (FIG. 4A). Methane production in all reactors increased exponentially in the first 15-20 days. After that, methane production in control reactors gradually decreased to the end of the experiment. In average, reactors with feather keratin produce 1.4 times more keratin than control reactors. The concentrations of volatile fatty acids (VFAs) including acetic acid, propionic acid and isobutyric acid in mixed liquor of all reactors were also monitored during the SBR operation. The profiles of these VFAs were shown in FIGS. 4B, C and D, correspondingly. In the first 10-15 days concentrations of all three organic acids are significantly higher. This could be due the presence of fermentable organic substrates in starting sludge. After their consumption, the concentration of each WA fluctuated within a certain range. Acetic acid fluctuated from 23 to 97 mg/L. No obvious difference in acetic acid concentration could be observed between reactors with feather keratin and the control reactors in the first 60 day. The average acetic acid concentration in reactors with feather keratin is 93 and 97 mg/L, respectively, higher than 75 and 68 mg/L in control reactors. The result suggests that addition of feather keratin stimulated production of acetic acid.

Figure 4C:
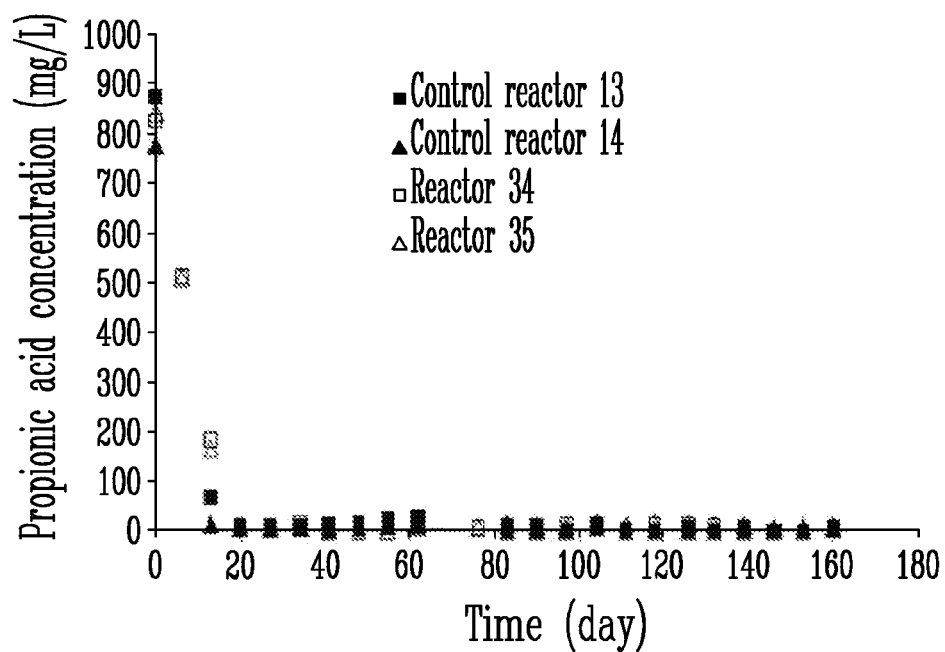
Figure 4D:
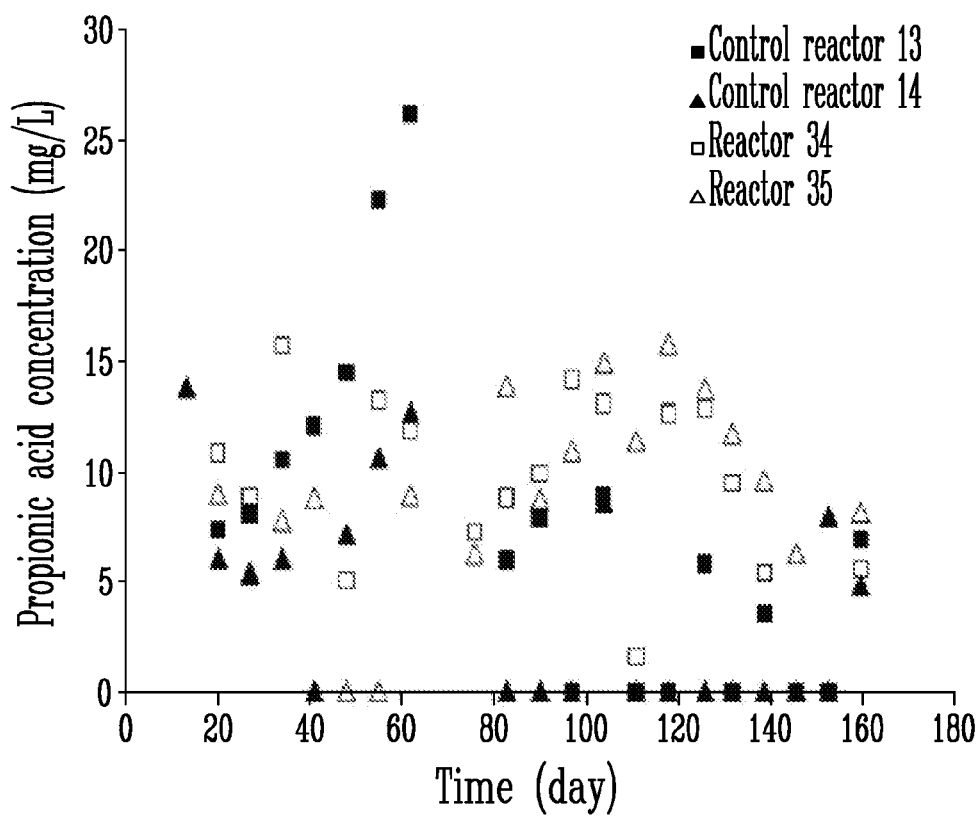
Figure 5A:
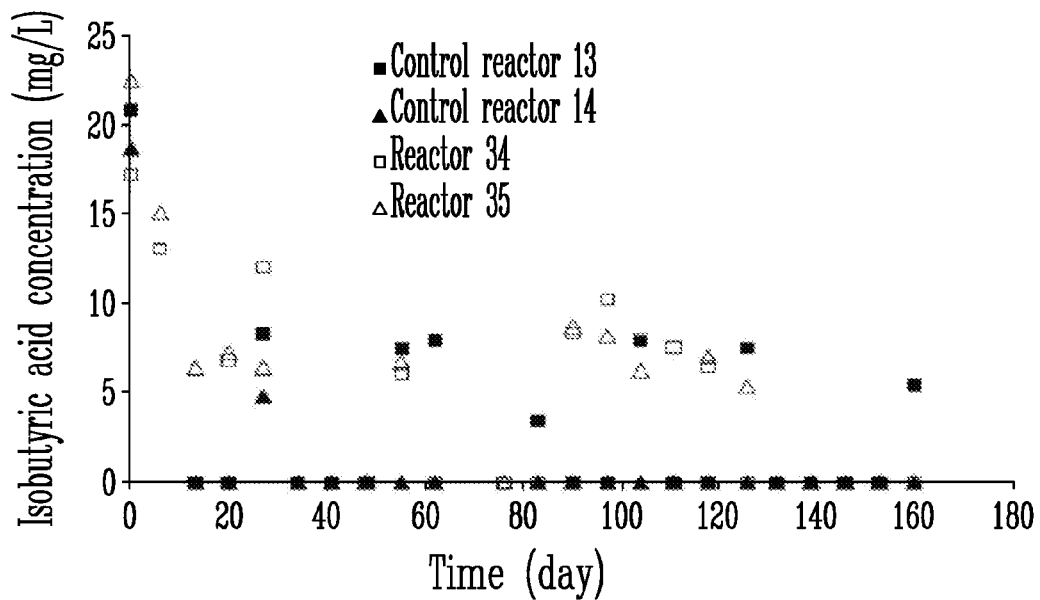
FIG. 5A illustrates the isobutyric acid concentration measured in reactors with (reactors 34 and 35) and without feather keratin (reactors 13 and 14).

Propionic acid concentration was also affected by adding feather keratin. As shown in FIG. 4C, propionic acid concentration in starting sludge is high. It gradually decreased in the first 15 days. After that, it fluctuated from 0 to 26 mg/L (see FIG. 4D). As observed in acetic acid profile, no significant difference in propionic acid production could be found between reactors with feather keratin and their control reactors in the first 62 days. After 72 days values of propionic acid concentration measured in reactors with feather keratin are mostly higher than those in control reactors. Addition of feather keratin did not significantly affect isobutyric acid concentration (see FIG. 5A). After 90 days, most values of isobutyric acid concentrations measured in reactors with feather keratin are higher than in those in their control reactors. The average concentration in reactors with feather keratin is 1.9 time of that in control reactors, indicating a positive effect of adding feather keratin.

Figure 5B:
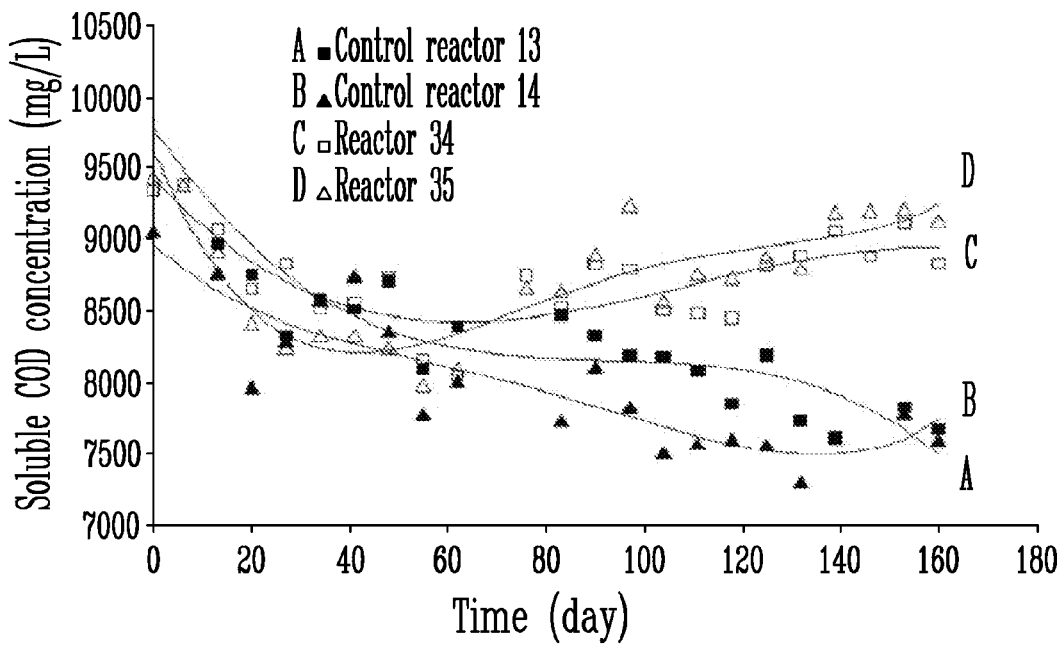
FIG. 5B illustrates the soluble chemical oxygen demand (SCOD) measured in reactors with (reactors 34 and 35) and without feather keratin (reactors 13 and 14).

Feather keratin also affects the concentration of soluble COD. As shown in FIG. 5B, SCOD in all reactors decreased gradually in the same trend in the first 60 days. Then, SCOD in control reactors kept decreasing to the end of experiment. SCOD in reactors with feather keratin, however, increased gradually to the end of the experiment. The average SCOD concentration in reactors with feather keratin were of 8757 mg/L, which is 1.1 times higher than that (8171 mg/L) measured in control reactors.

Figure 6A:
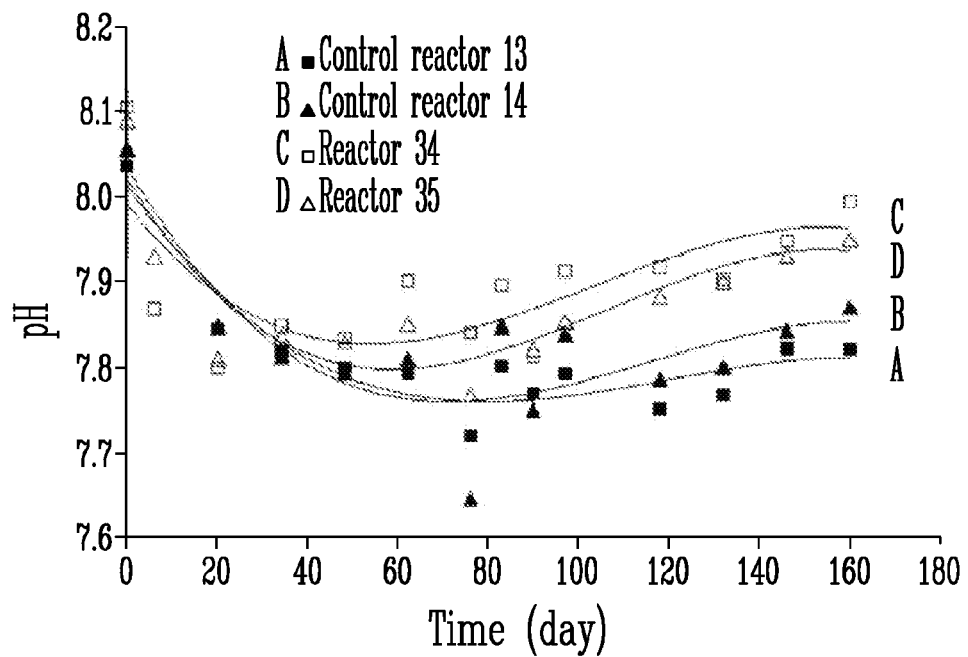
FIG. 6 illustrates in (A) the pH profiles and in (B) the alkalinity profiles measured in reactors with (reactors 34 and 35) and without feather keratin (reactors 13 and 14).
Figure 6B:
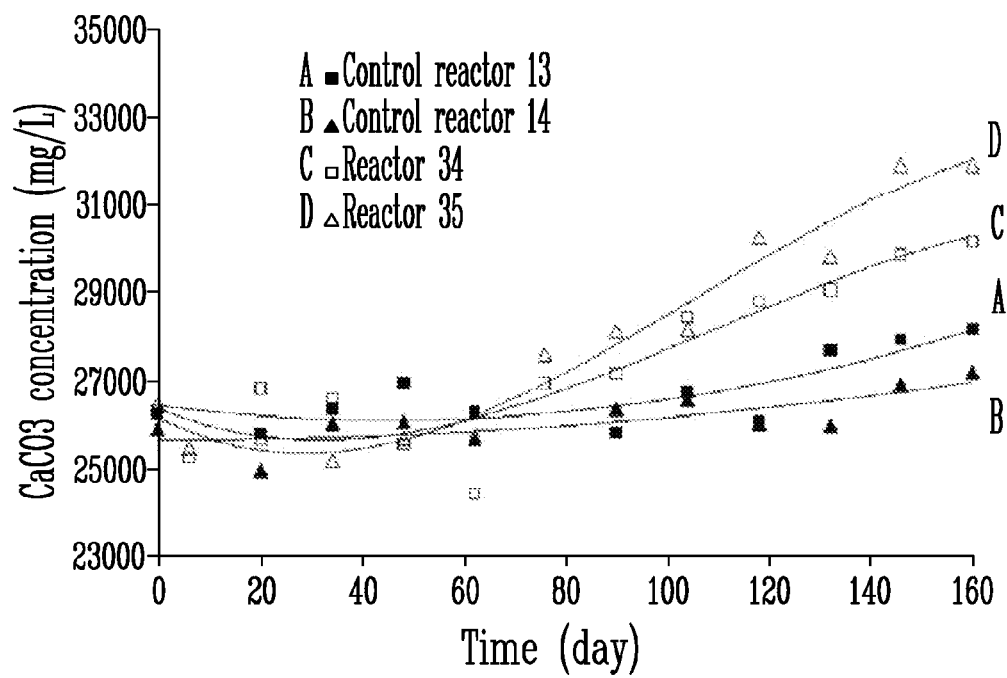

Feather keratin also affected mixed liquor pH in SBR reactors. As shown in FIG. 6A, pH in all reactors gradually decreased from 8.0-8.1 to 7.8 in the first 50 days. After that, all the pH values measured in reactors with feather keratin are 0.05-0.10 higher than those measured in control reactors. Feather keratin significantly affected alkalinity. As shown in FIG. 6B, in the first 60 days alkalinity in all reactors mostly fluctuated between 25000 and 27000 mg/L. After that, alkalinity measured in control reactors still kept the same trend to the end of the experiment. However, alkalinity in reactors with feather keratin gradually increased up to 28839 and 28171 mg/L.

Figure 7A:
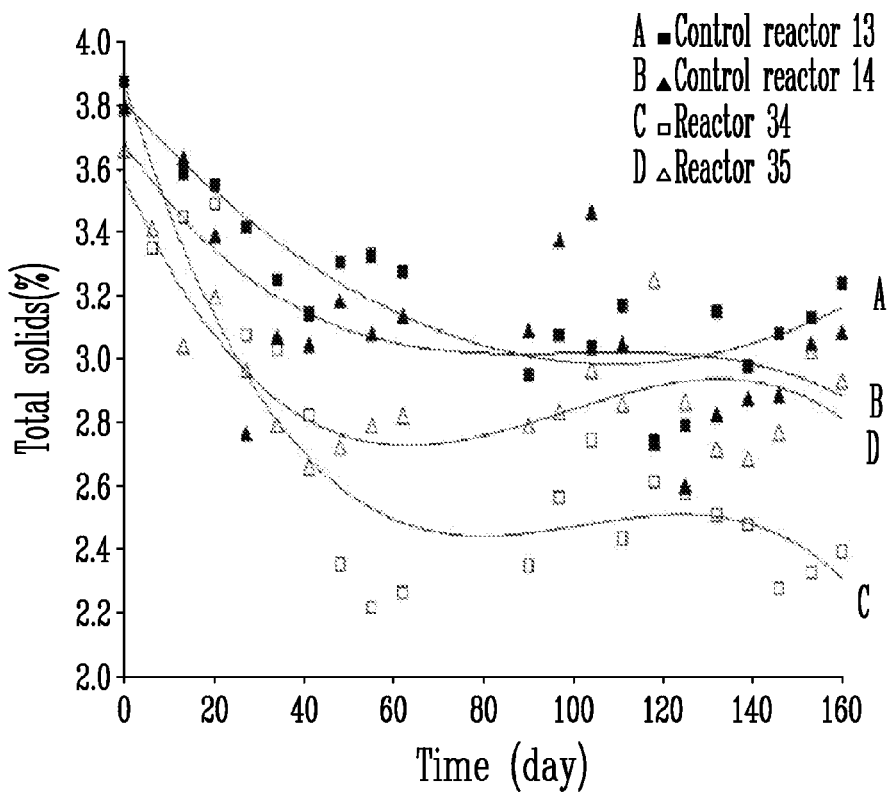
FIG. 7 illustrates in (A) the total solids (TS), (B) volatile solids (VS) and (C) volatile suspended solids (VSS) profiles measured in reactors with (reactors 34 and 35) and without feather keratin (reactors 13 and 14).
Figure 7B:
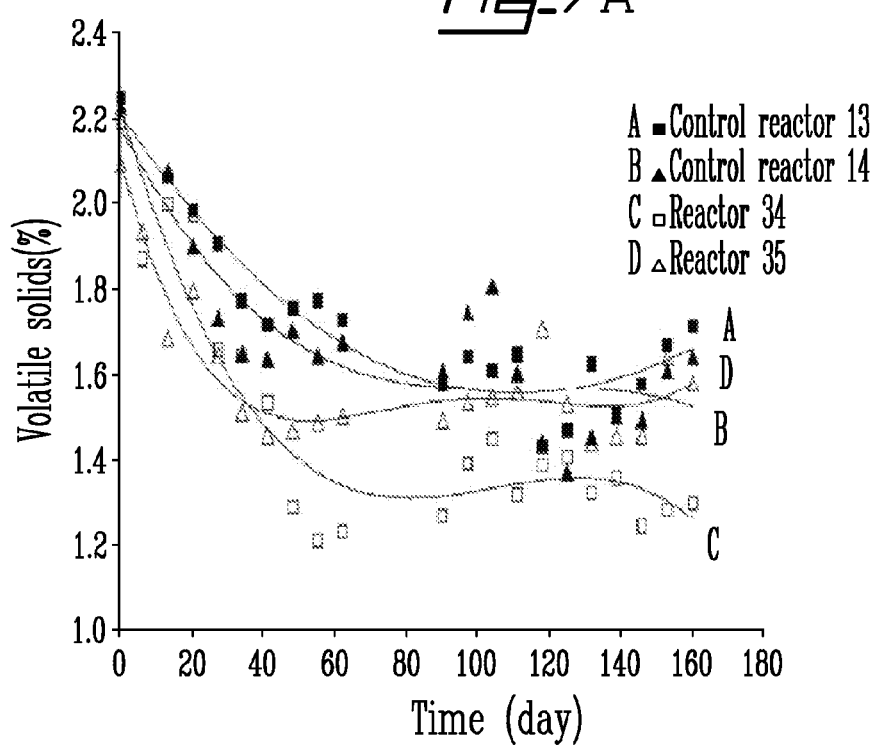
Figure 7C:
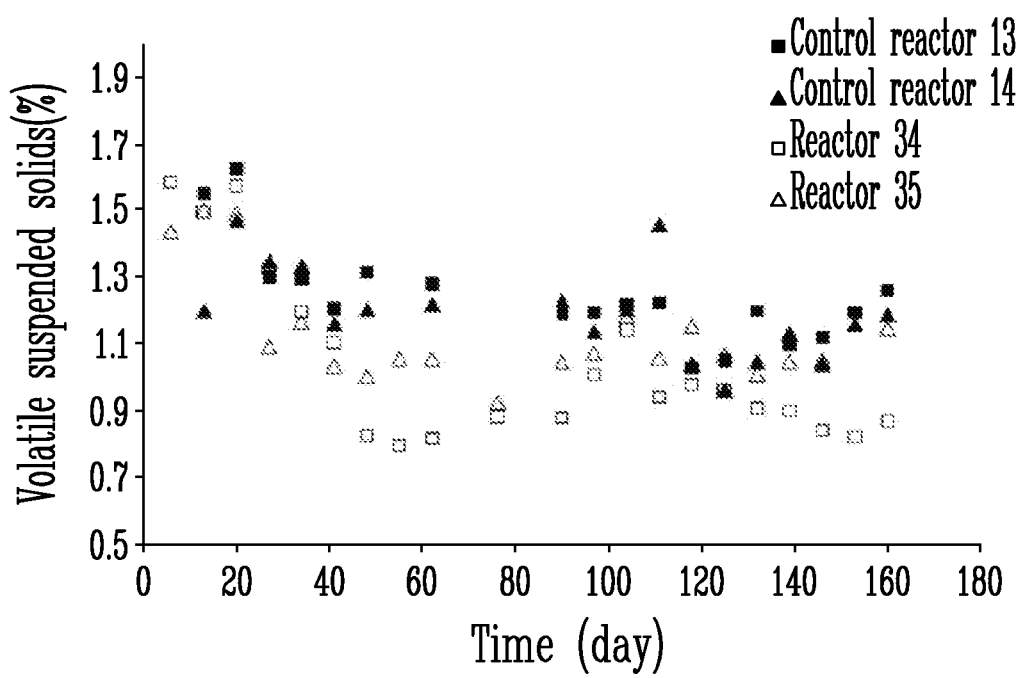

Feather keratin, in addition, also affected the TS profiles. As shown in FIG. 7A, TS in all control reactors gradually decreased in the first 80 days then fluctuated within a certain range. Generally, TS in reactors with feather keratin decreased at a faster speed than in control reactors. TS values measured in reactors with feather keratin are mostly lower than those measured in control reactors. In average, TS value in control reactors is 1.1 times higher than in reactors with feather keratin. Similar profiles observed in TS also exist in VS and VSS profiles. VS and VSS in all reactors gradually decreased in the first 60-80 days then fluctuated within a certain range. The significant difference is that VS and VSS in reactors with feather keratin decreased to a lower level than in control reactors. VS and VSS values measured in reactors with feather keratin are mostly lower than in reactors with feather keratin.

Feather keratin in bags decreased in AD-SBRs fed with swine manure. The decrease observed is most due to microbial activity, i.e. keratin hydrolyzing microorganisms excreting keratinase and hydrolyzing the feather keratin in bags. Keratin added in AD-SBRs fed with swine manure did not affect negatively the performance of AD-SBRs. It improved the biogas production and reduced biomass production of the ADSBRs.

BODIPY fluorescence exoenzyme staining methods were used to label and visualize keratin hydrolytic microorganisms (KHOs). BODIPY FL casein was first applied to samples of feather bags in bioreactors. After 30 mm of staining, fluorescence on bacteria with a morphotype of rod was observed on a weak fluorescent background. No other morphotype was observed during 180 min staining. Sampling and microscopic examination were carried out every 15 min. The background fluorescence, however, increased with time. The same staining was carried out on samples from all the reactors with or without feather keratins added. When the samples (fluids of feather bags or mixed liquor) from different AD-SBRs were heated at 100° C. for 10 min (as negative controls), no fluorescence (including background fluorescence) could be observed, indicating the fluorescence observed is due to microbiological activity. To specifically label the KHOs in AD-SBRs and not the consumers of labelled hydrolysates which could be also stained in BODIPY FL staining, a set of inhibitors (Xia et al., 2008, FEMS Microbiology Ecology, 66: 462-471) was added in all the staining incubations. Iodoacetate, fluoroacetate, and azide were added to inhibit the glycolysis, the TCA cycle, and the electron transport chain, respectively. The individual inhibitors were added at concentrations at which the energy metabolisms of all the microorganisms in AD-SBRs were effectively inhibited (Xia et al., 2008, supra). In the presence of the inhibitors, all fluorescing rods observed previously were still observed; the difference being the number of KHOs remarkably reduced after inhibition. Therefore, the bacteria positively stained are putative KHOs responsible for the degradation of feather keratin observed in these AD-SBRs.

Figure 8A:
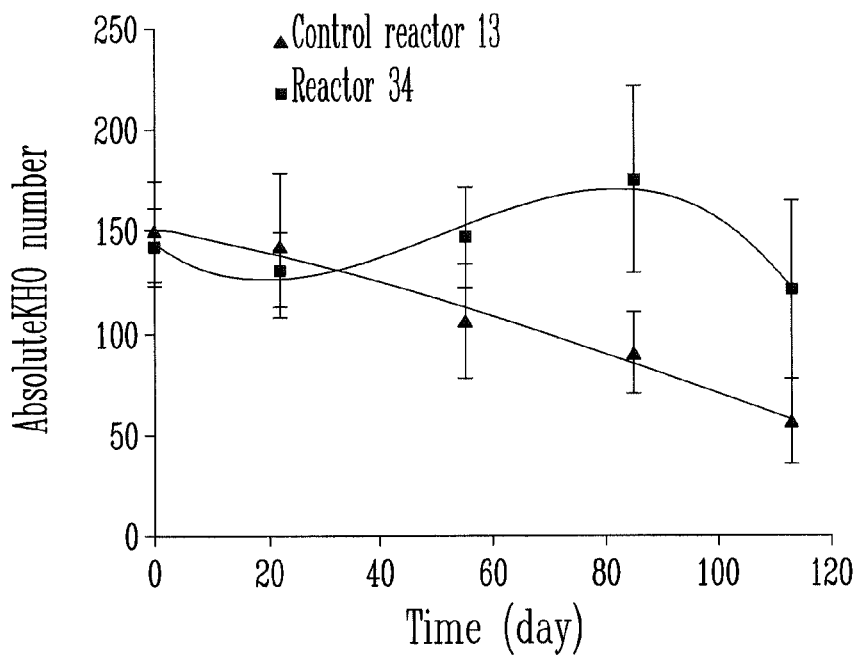
FIG. 8 illustrates in (A) the amount of keratin hydrolyzing organisms (KHOs) present in the mixed liquor of control reactor 13 and reactor 34 with feather keratin and in (B) the correlation measured between the degradation of feather keratin and the number of KHOs.

The relative numbers of KHOs in mixed liquor of AD-SBRs were estimated by keeping all the procedure including sampling, sample preparation, microscopic examination, image capture and image analysis constant. The results are listed in Table 1. As shown in FIG. 8A, the numbers of KHOs in control reactor gradually decreased from 150 at day 0 to 56 at day 113. The number of KHOs in reactor with feather keratin slightly decreased in the first 20 days from 142 to 131, and then gradually increased up to 175 at day 85 before decreasing to 121 at day 113.

TABLE 1

Degradation of feather keratin and number of KHOs in AD-SBRs fed with swine manure slurry

| Time (day) | Weight decrease of feather keratin in bags (g) | | Decrease percentage of feather keratin in bags (%) | | Number of KHOs* |
|---|---|---|---|---|---|
| | Reactor 34 | Reactor 35 | Reactor 34 | 35 | Reactor (34) |
| 0 | 31.76 ± 0.28 | 31.5 ± 0.44 | 0 | 0 | 0 |
| 22 | 25.17 ± 2.03 | 23 ± 0.44 | 21 | 27 | 12 ± 38$^d$ |
| 55 | 16.12 ± 1.83 | 14.26 ± 0.01 | 51 | 55 | 49 ± 10 |
| 85 | 9.24 ± 0.11 | 8.37 ± 0.26 | 71 | 73 | 101 ± 37 |
| 113 | 4.54 ± 0.99 | 5.63 ± 0.23 | 86 | 82 | 81 ± 28 |

Figure 8B:
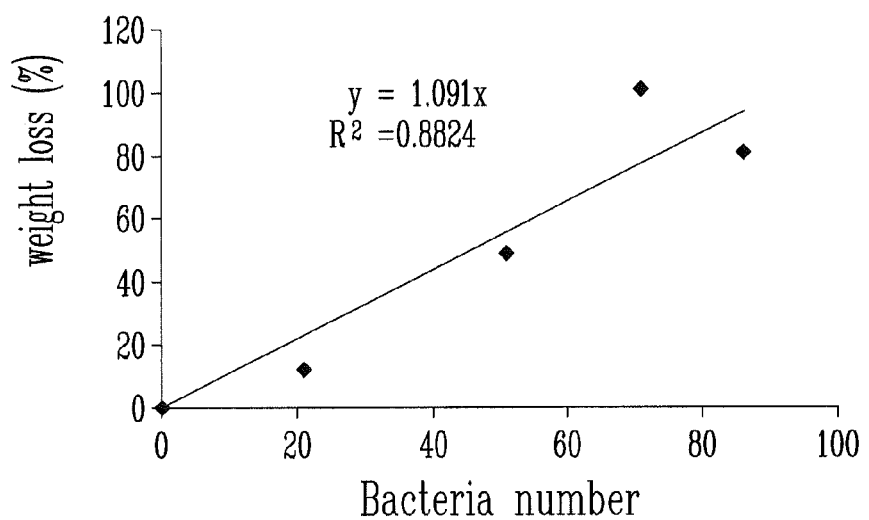

As the number of KHOs increased in the feather bags as well as their activity, a significant amount of soluble keratin was released into the mixed liquor. Afterwards, KHOs in mixed liquor started to grow and multiply and reached a high abundance (101) at the end of third month and decreased after that, but still kept a relative high number (81) at the end of four month because soluble keratin or its hydrolysates were kept released into the mixed liquor because once a bag was taken out from a SBR, a new feather bag was put in. The relative numbers of KHOs inside feather keratin bags of reactor were also counted. In order to effectively harvest KHOs inside feather bags for BODIPI FL casein staining, numbers of bacterial cells obtained after centrifugation at 800 g, 1000 g, 1500 g, 2000 g, 2500 g or 3000 g were estimated. The bacteria obtained were stained with DAPI and their number was estimated microscopically. The results are listed in Table 1. A positive correlation between the number of KHOs inside feather bags and degradation of feather keratin was observed (see FIG. 8B). It confirms that degradation of feather keratin observed in bags was due to the activity of KHOs visualized but not due to other physiochemical reactions. The highest number of KHOs (101 cells) was observed in the third month (day 85), corresponding to the highest degradation rate (71% in bio34 and 73% in bio35; Table 1) of feather keratin. Both the highest enrichment of KHOs and degradation rate were achieved in the third month. A slight decrease in the number of KHOs was observed at day 113. All results show that the hydrolysis rate is a limiting step for feather keratin degradation in AD-SBRs fed with swine manure. These evidences also confirmed that the degradation of feather keratin was due to exo-enzyme secreted by KHOs rather than chemical and physical activities in AD-SBRs fed with swine manure.

BODIPY FL casein staining was also carried out on original sludge samples from a commercial pig farm and a cattle slaughter house. The results are also shown in Table 2.

TABLE 2

KHOs in different AD-SBRs environments

| Sample source | Sample | Chicken keratin added | Source stained | Presence of KHOs$^f$ |
|---|---|---|---|---|
| Commercial pig farm | Raw swine manure | NO | Mixed liquor | − |
| Commercial cattle slaughterhouse farm | Raw slaughter house sludge | NO | Mixed liquor | − |
| Lab-scale semi industrial bioreactor 17 | Treated swine manure$^b$ | NO | Mixed liquor | + |
| Lab-scale semi industrial bioreactor 17a | Treated slaughterhouse sludge$^c$ | NO | Mixed liquor | + |
| Lab-scale bioreactor 13 | Inoculums of swine manure$^d$ | NO | mixed liquor | + |
| Lab-scale bioreactor 14 | Inoculums of swine manure | NO | mixed liquor | + |
| Lab-scale bioreactor 34 | Inoculums of swine manure | in bags | inside of bags | + |
| Lab-scale bioreactor 34 | Inoculums of swine manure | in bags | mixed liquor | + |
| Lab-scale bioreactor 35 | Inoculums of swine manure | in bags | inside of bags | + |
| Lab-scale bioreactor 35 | Inoculums of swine manure | in bags | mixed liquor | + |
| Anaerobic bucket 1$^a$ | Water | in bags | inside of bags | − |
| Anaerobic bucket 1 | Water | in bags | Mixed liquor | − |
| Lab-scale bioreactor 13A | Inoculums of slaughterhouse sludge$^e$ | NO | mixed liquor | + |
| Lab-scale bioreactor 13B | Inoculums of slaughterhouse sludge | NO | mixed liquor | + |
| Lab-scale bioreactor 15 | Inoculums of slaughterhouse sludge | in mixed liquor | mixed liquor | + |
| Lab-scale bioreactor 16 | Inoculums of slaughterhouse sludge | in mixed liquor | mixed liquor | + |

No positive signal was observed. The KHOs observed in the AD-SBRs were not present. BODIPY FL enzyme staining was also used to detect any potential KHOs present in an anaerobic bucket in which feather bags were incubated with distilled water under same condition as other AD-SBRs. No KHOs were present in neither inside of bags nor mixed liquor (Table 2).

Feather keratin degradation in AD-SBRs is due to activity of microorganisms. Microorganisms capable of hydrolyzing feather keratin (keratin hydrolyzing organisms, KHOs) are present in the swine manure used to feed the SBR reactors. When bags containing feather keratin are put into the reactors fed with swine manure, KHOs penetrate with liquid into the bags and attach on the feather particles. Then, the KHOs excrete extracellular keratinase and hydrolyze crystal feather keratin into soluble keratin, oligopeptides and amino acids. Once the amino acids and/or oligopeptides are available, KHOs grow and multiply until their number and activity reach a certain level, when amino acids and oligopeptides start to accumulate. The amino acids, oligopeptides and even soluble keratin inside are driven outside of the bags by chemical gradient, where they are used by microorganisms including hydrolyzers, fermenters, methanogenes and sulfate reducing bacteria. This process take at least 30-40 days. During this period, therefore, no significance difference in gas production, gas production rate, methane production, VFAs, pH, alkalinity, TS, VS and VSS is observed between the reactors with feather keratin and the control reactors without feather keratin.

Once the extra amino acids and oligopeptides are obtained, microorganisms in mix liquor use them as nitrogen sources to grow and/or increase activity. Hydrolysis and fermentation activities in the reactors are improved; therefore, a higher VFA (mainly acetic acid) concentration is detected in reactors with feather keratin. A high VFA level further stimulates the activity of methanogens. Methanogens convert most of VFAs produced into methane and $CO_2$. Consequently, as observed, more gas and methane, are produced in reactors with feather keratin than in control reactors, which result in a low TS, VS and VSS values as a significant part of carbon source in the mixed liquor has been transferred in gases. Because more $CO_2$ is produced in reactors with feather keratin, a higher alkalinity level is detected in these reactors than in control reactors without feather keratin.

Figure 9A:
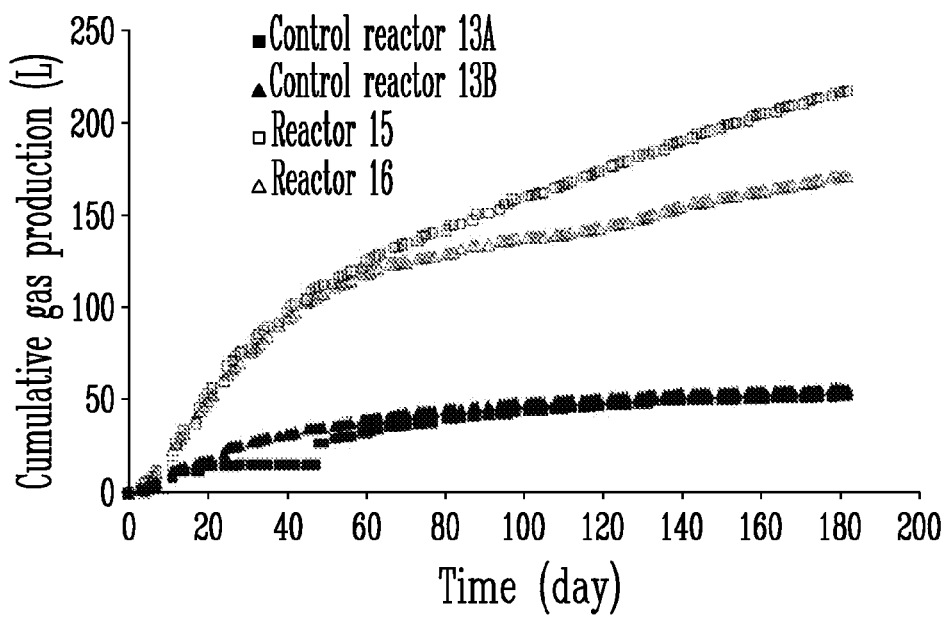
FIG. 9 illustrates in (A) the cumulative gas production and in (B) the daily gas production measured in reactors with (reactors 15 and 16) and without feather keratin (reactors 13A and 13B).

Addition of feather keratin affects the gas production. As shown in FIG. 9A, cumulative gas production in reactors with feather keratin increased exponentially in the first 40 days (up to ca 100 at day 40), while in control reactors gas production gradually increased to 32 L at day 40. In average, cumulative gas production in reactors with feather keratin is 6.7 times more than that produced in control reactors.

Figure 9B:
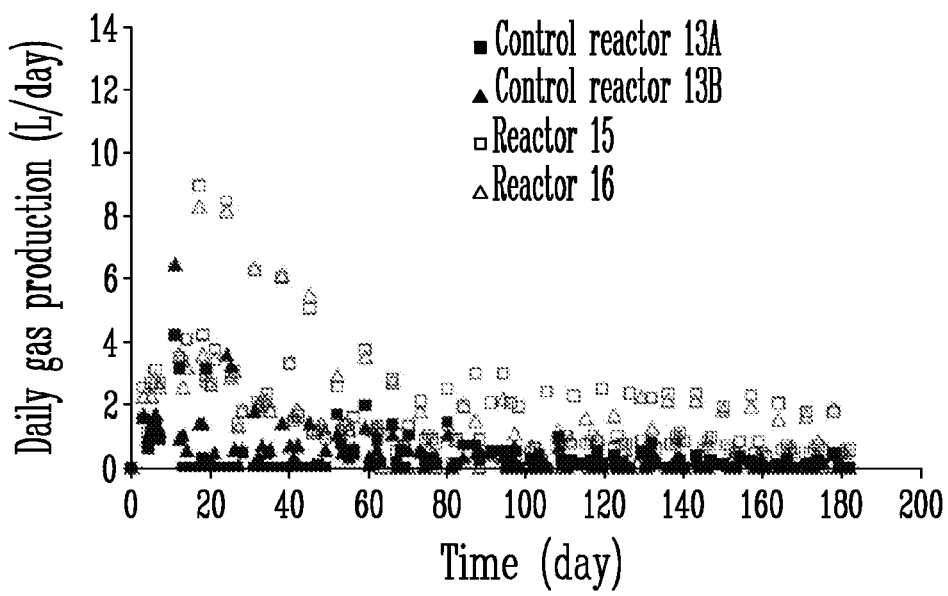

The effect of feather keratin on gas productions could also be seen on daily gas production rates. As shown in FIG. 9B, gas production rates in all reactors fluctuate within 0-12 L/day in the first 60 days. After that, gas production rates in control reactors gradually decrease to less than 1 L/day. The gas production rates in reactors with feather keratin, however, still fluctuated within 0-2.5 L/day after the first 60 days and remained the same trend to the end of experiment. The average rate measured in reactors with feather keratin is 3.1 times higher than that observed in control reactors.

Figure 10A:
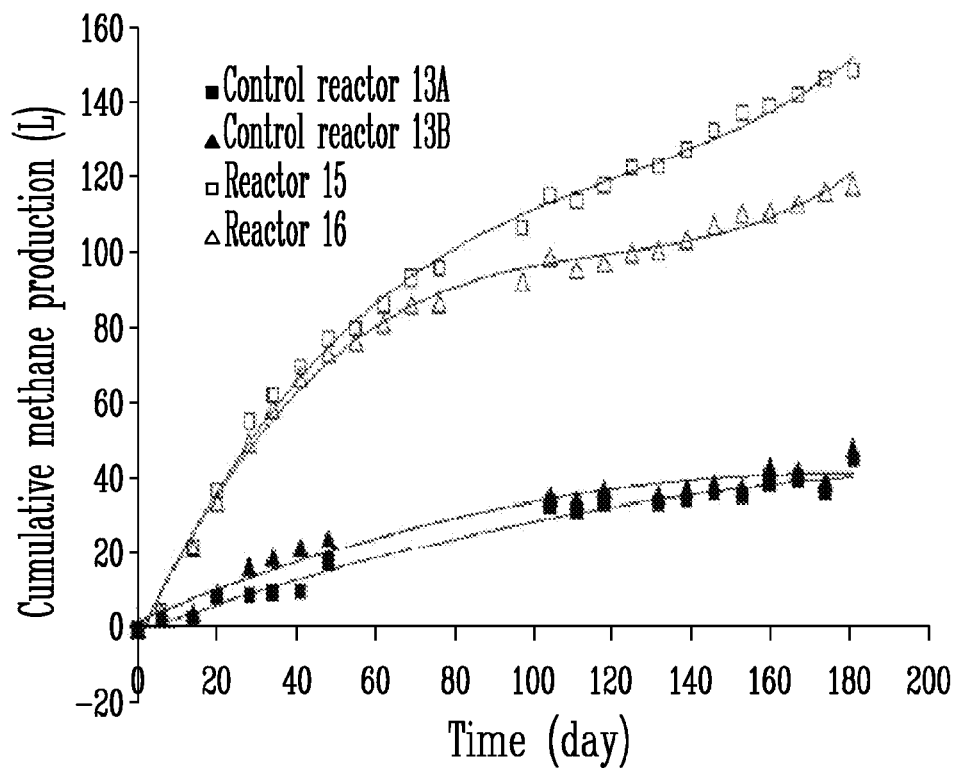
FIG. 10 illustrates in (A) the cumulative methane production, (B) acetic acid concentrations, (C) propionic acid concentrations and (D) isobutyric acid concentrations measured in reactors with (reactors 15 and 16) and without feather keratin (reactors 13A and 13B).
Figure 10B:
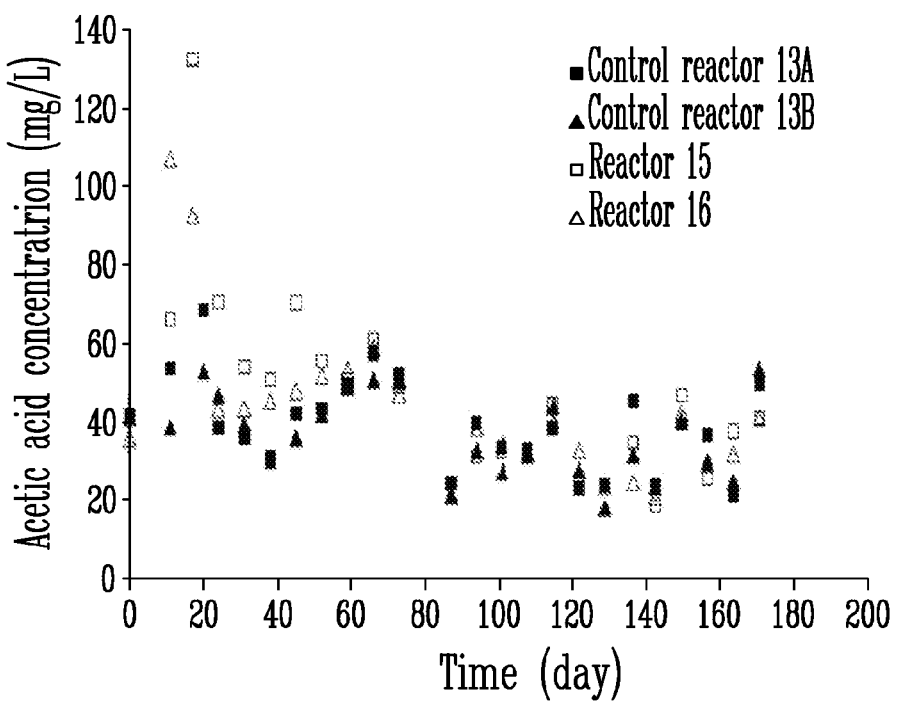
Figure 10C:
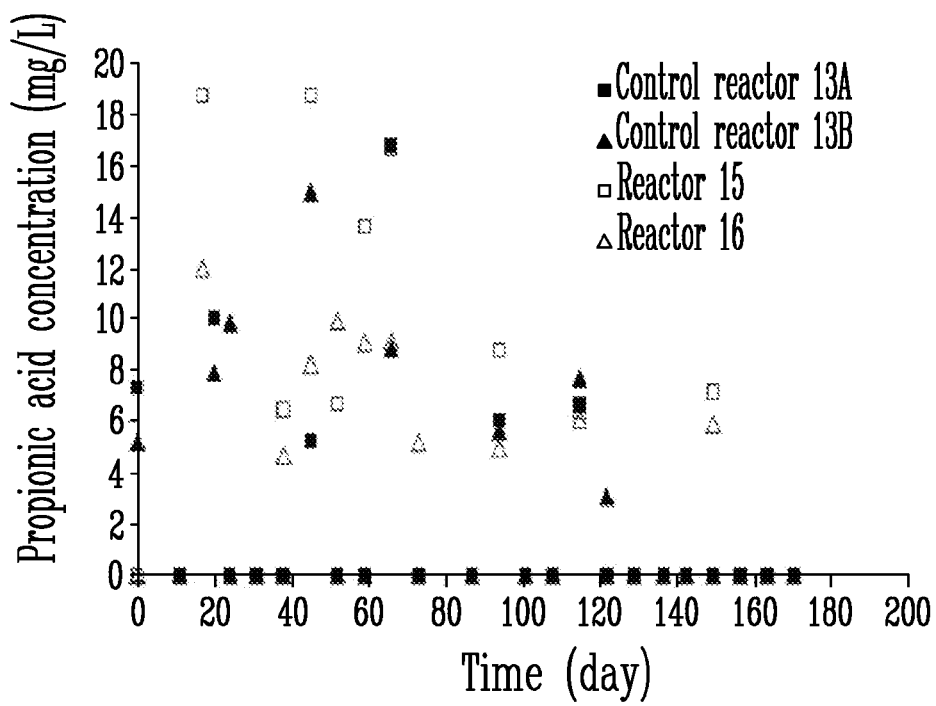
Figure 10D:
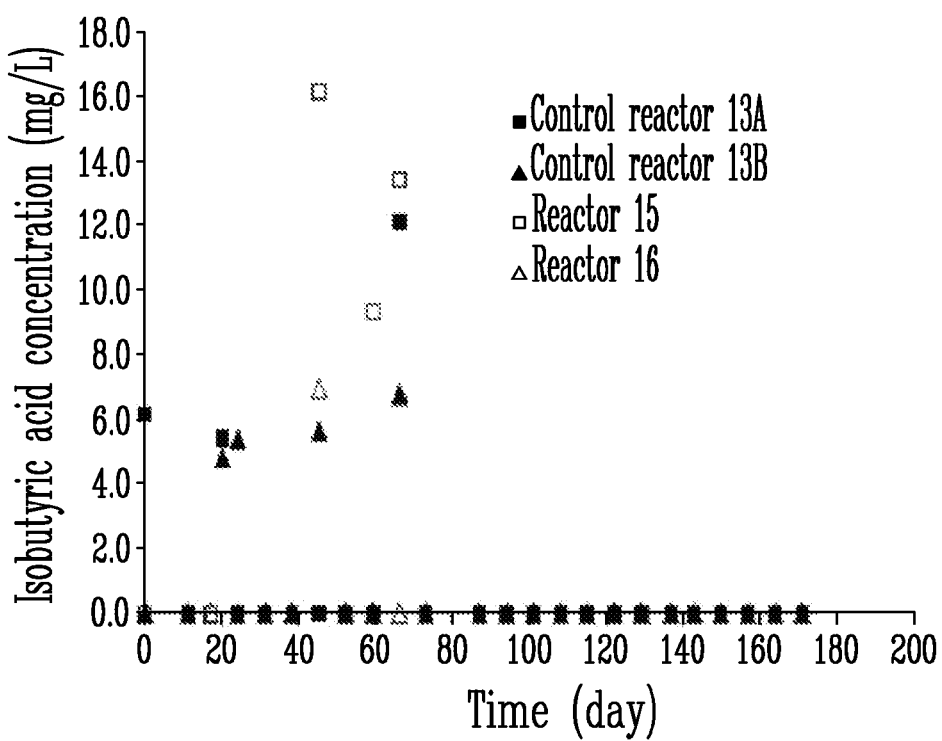

Effect of feather keratin addition on gas production could also be seen on the cumulative methane production profiles (FIG. 10A). Methane production in reactors with feather keratin increased at much higher speeds than that in control reactors. The average cumulative methane production in reactors with feather keratin is 3.4 times more than that produced in control reactors. As shown in FIG. 10B, acetic acid concentrations measured in all reactors with or without feather keratin fluctuates between 18-70 mg/L during all experimental period except in the first 15 days where a much higher acetic acid concentration was detected in reactors with feather keratin. Similarly, no significant difference in propionic acid as (FIG. 10C) well as isobutyric acid concentration (FIG. 10D) could be detected between reactors with feather keratin and control reactors. The concentrations of propionic acid varied from 0 to 19 mg/L and the concentrations of isobutyric acid varied between 0-16 mg/L. Therefore, feather keratin added does not significantly affect VFA production.

Figure 11:
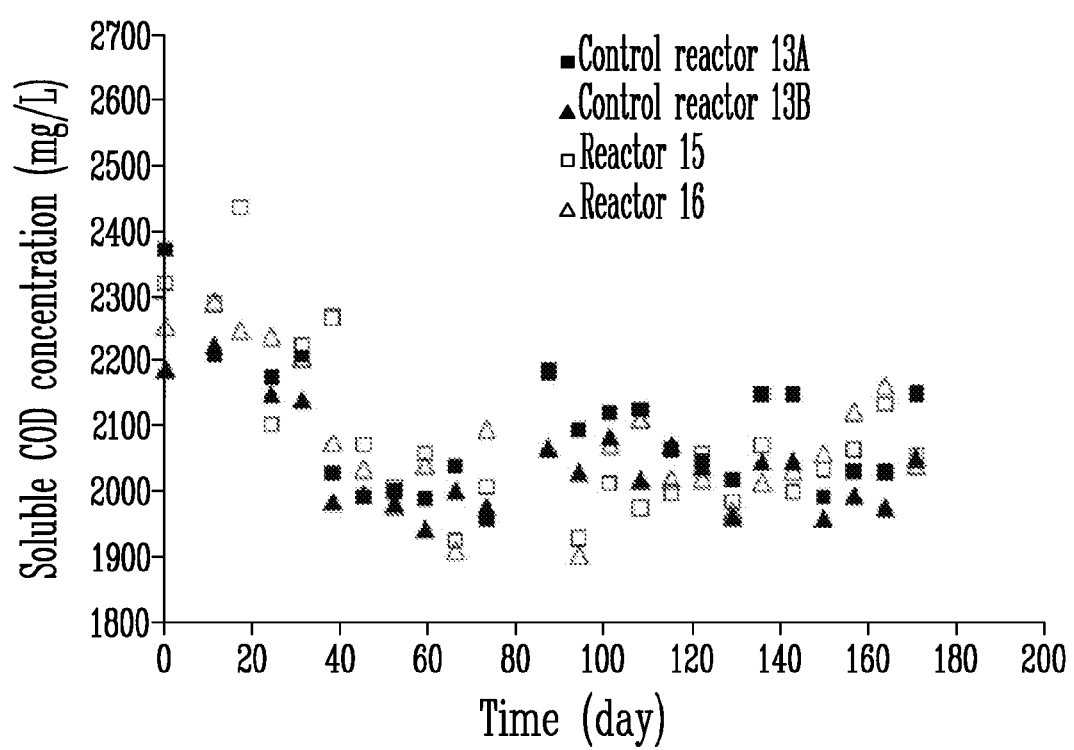
FIG. 11 illustrates the soluble chemical oxygen demand (SCOD) measured in reactors with (reactors 15 and 16) and without feather keratin (reactors 13A and 13B).

Addition of feather keratin did not significantly affect the soluble COD. As shown in FIG. 11, SCOD in all reactors decreased gradually in the same trend in the first 30 days before fluctuating from 1912 to 2185 mg/L.

Figure 12A:
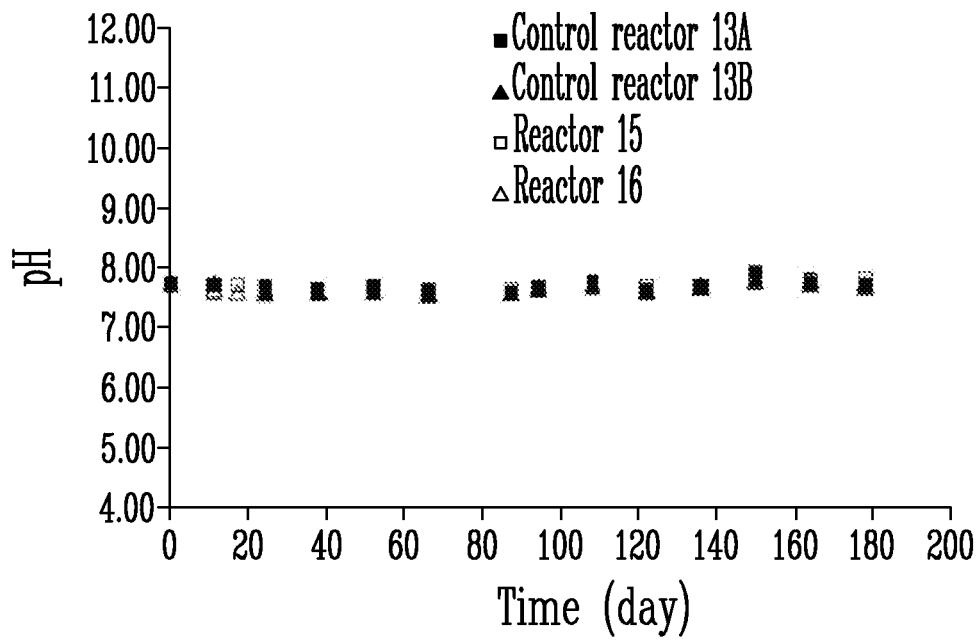
FIG. 12 illustrates in (A) the pH profiles and in (B) the alkalinity profiles measured in reactors with (reactors 15 and 16) and without feather keratin (reactors 13A and 13B).
Figure 12B:
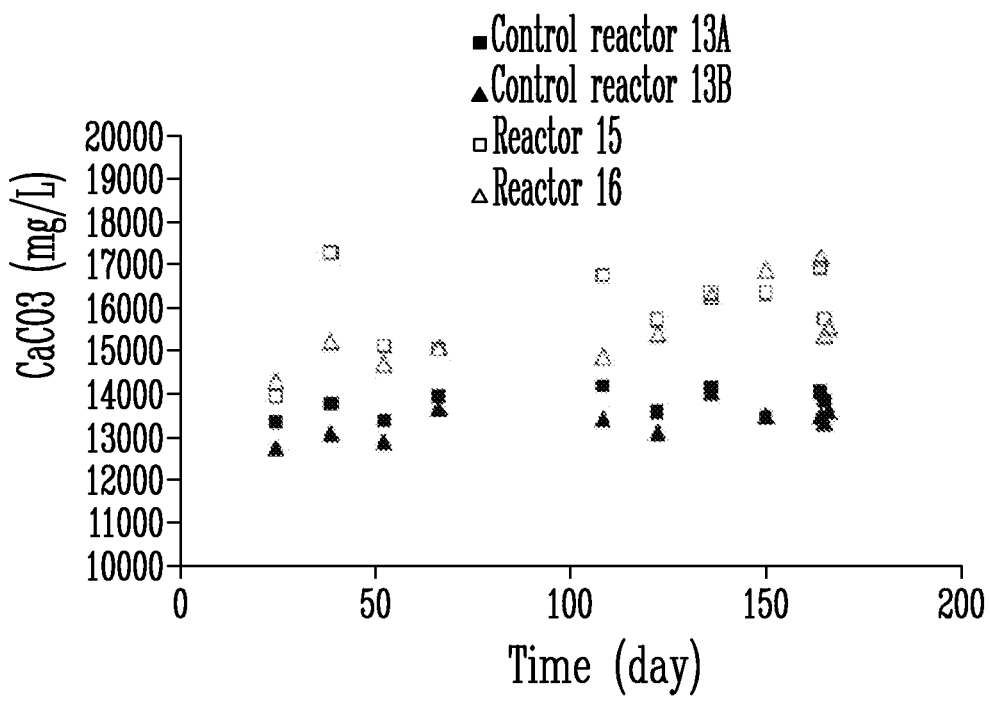

Similarly, addition of feather keratin did not significantly affect mixed liquor pH (FIG. 12A). Adding feather keratin, however, at least slightly affected alkalinity. $CaCO_3$ measured in reactors with feather keratin (FIG. 12B) are slightly higher than those measured in control reactors. The average $CaCO_3$ concentration in reactors with feather keratin is 15578 mg/L, higher than 13606 mg/L observed in control reactors.

Figure 13A:
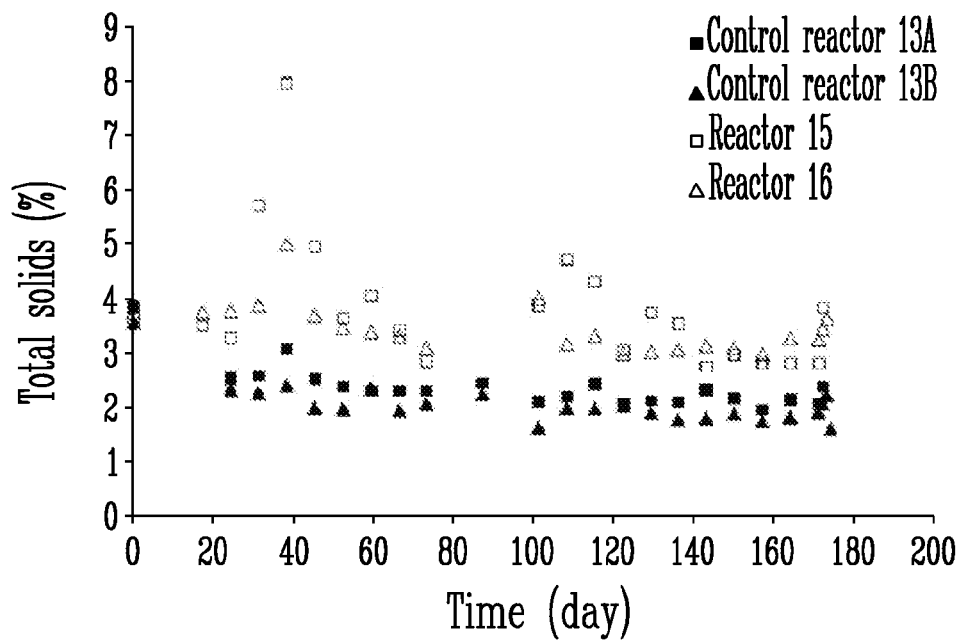
FIG. 13 illustrates in (A) the total solids (TS), (B) volatile solids (VS) and (C) volatile suspended solids (VSS) profiles measured in reactors with (reactors 15 and 16) and without feather keratin (reactors 13A and 13B).
Figure 13B:
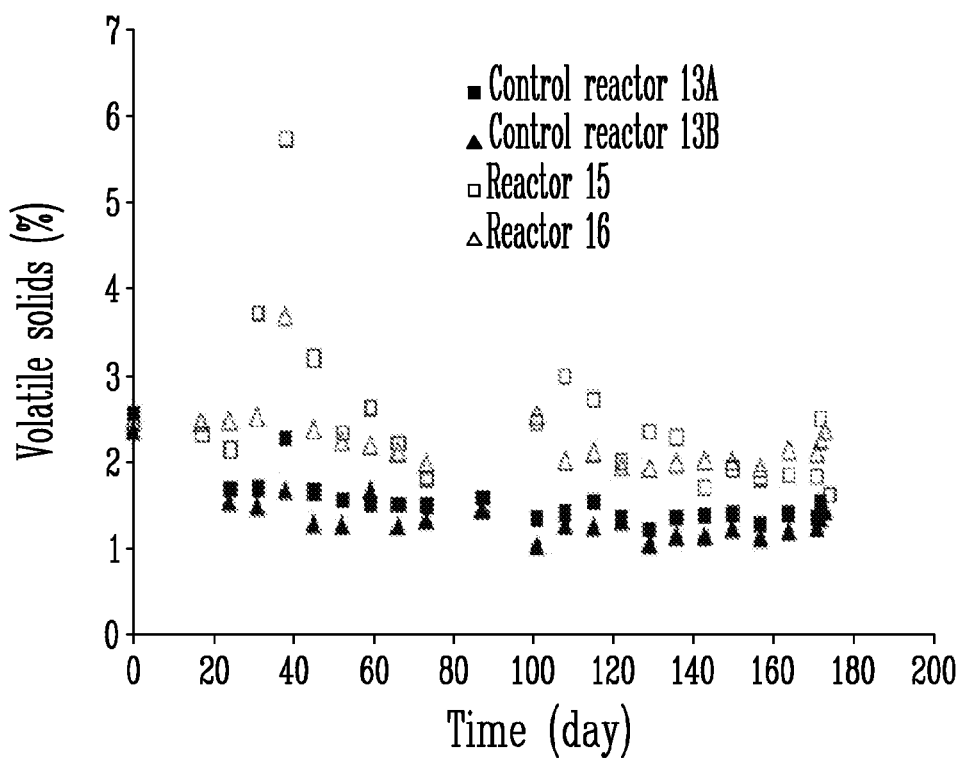
Figure 13C:
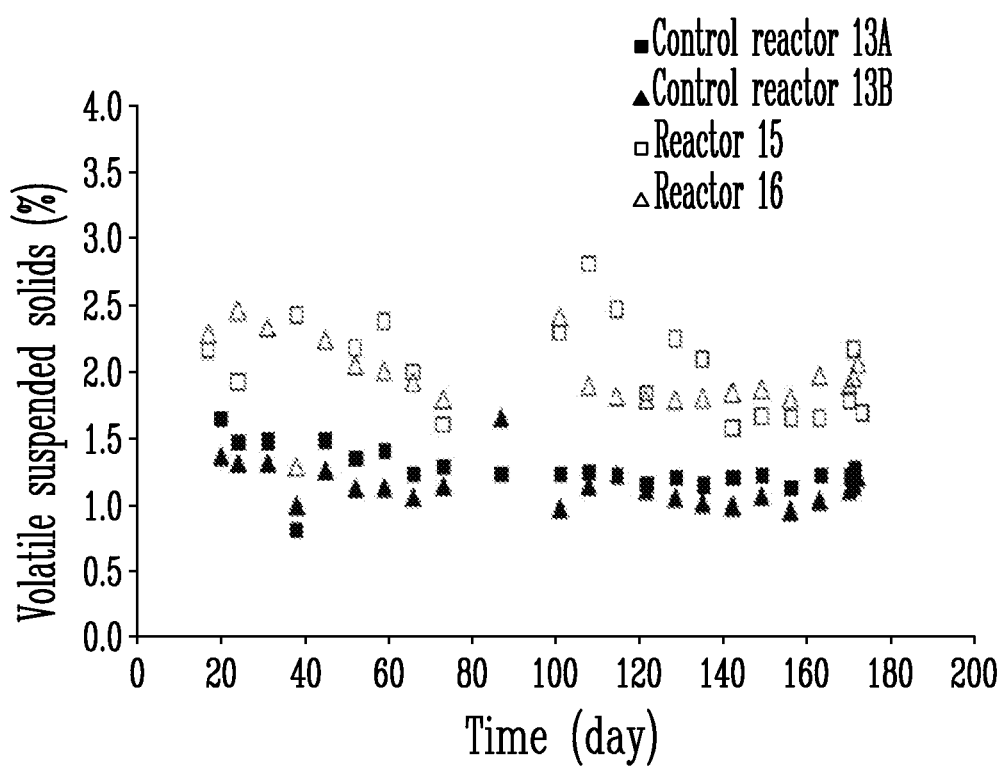

TS profiles in reactors with feather keratin are also different from those in control reactors without feather keratin. As shown in FIG. 13A, TS in the two control reactors gradually decreased from day 0 to day 20 then fluctuated within 1.7-3.1%. However, TS in reactors with feather keratin did not decrease and fluctuated between 2.8-7.9%. In average, TS value in reactors with feather keratin is 3.7%, being 1.6 times higher than 2.3% measured in control reactors. The VS (FIG. 13B) and VSS (FIG. 13C) profiles observed is similar to the TS profiles. VS and VSS values measured in reactors with feather keratin are all higher than those measured in control reactors, in average being 1.6 (VS) and 1.7 (VSS) times, respectively, higher than those measured in control reactors.

Figure 14:
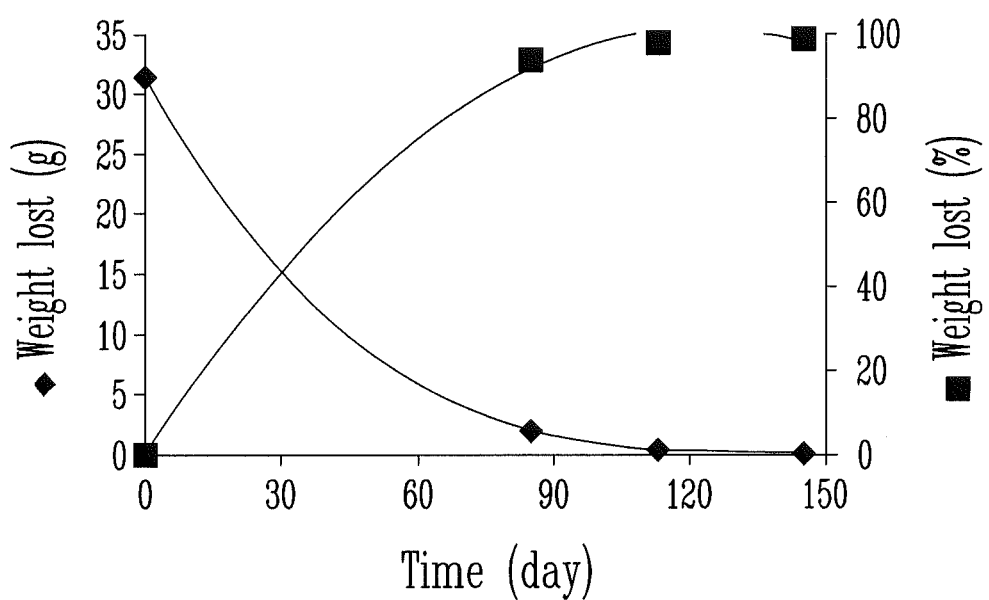
FIG. 14 illustrates the biodegradation of feather keratin in a PAD seeded with swine manure (run 2).

Feather keratin degradation in the PAD seeded with swine manure and added with feather bags (feather PAD) was measured to a level of efficacy of 99% after 150 days (see Table 5, FIG. 14). It is disclosed that keratinase is an inducible enzyme which can be induced in the presence of keratin. Therefore a proper enrichment process increases efficiency of the degradation of keratin in PADs.

Bovine hoof keratin degradation in the PAD seeded with swine manure and added with hoof bags is also disclosed. In all individual nylon bags, 86% of the hoof keratin was degraded after 113 days (see Table 6, FIG. 15).

Therefore, it is demonstrated herein that feather keratin and bovine hoof can be hydrolyzed and degraded in AD-SBRs fed with at least swine manure and slaughterhouse sludge. Addition of feather keratin improves the operation of AD-SBRs improving the biogas production. Prions in contaminated carcasses can thus be treated in AD-SBRs, since feather keratin and/or bovine hoof and prions are similar in their structure. The enzymatic breakdown of prions would most importantly help revive the use of animal meal as feed.

The present disclosure will be more readily understood by referring to the following examples which are given to illustrate embodiments rather than to limit its scope.

EXAMPLE 1

Feather Preparation and Characterization

Freshly plucked white chicken feathers were collected from a slaughterhouse (rue Principale, Saint-Anselme, Québec) that processes 900,000 chickens per week; and transferred to laboratory as soon as possible. The chicken feathers were aliquot (2 Kg) into clean normal cotton bags and washed in a washing machine (delicate wash). The feather samples were subsequently dried at 45° C. in a Unithern™ drier (Construction, CQLTD, England) until a constant weight was reached. They were cut and ground in a mill through a 4 mm screen. After that, the feather samples were aliquot (around 33 g each) into nitrogen-free polyester forage bags with a pore size of 50 microns (ANKOM Technology, 2052 O'Neil Road Macedon, N.Y. 14502, USA), sealed with plastic tie wraps and washed again in washing machine using the same condition to get rid of as much dusts as possible. Finally, the washed feather bags were dried again at 45° C. until their weights was constant. Feather bags were then attached into a steel stick and ready to be put into the bioreactors.

The feather samples ground were characterized physically and chemically in following ways. Total chemical oxidation demands (TCOD), ash content and organic matter content were determined according to the standard methods (APHA, 1992, In: Greenberg, A. E., Clesceri, L. S., Eaton, A. D. (Eds.), Standard Methods for the Examination of water and wastewater. American Public Health Association, Washington D.C.). Total Kjeldahl nitrogen (TKN) and ammonia-nitrogen were determined with a Tecator 1030 Kjeltec autoanalyser (Tecator A B, Hoganas, Sweden) following macro-Kjeldahl method described standard methods. Protein concentration was calculated by multiplying the difference between TKN and ammonia-N with 6.25 (AOAC, 1984, In: Williams, S., Baker, D. (Eds.), Official Methods of Analysis of the Association of Official Analytical Chemists, Arlington, Va.). Fat content was determined according to Schrooyen et al. (Schrooyen et al., 2000, Journal of Agricultural and Food Chemistry, 48: 4326-4334). Chicken feather samples (30 g) were Soxhlet extracted for approximately 12 h with petroleum ether (boiling range 40-60° C.) and the fat extracted was measured (Schrooyen et al., 2000, supra).

Amino acid concentration was determined following the isotope dilution method described by Calder et al. (Calder et al., 1999, Rapid Communications in Mass Spectrometry, 13: 2080-2083). Briefly, raw feather samples were hydrolysed with 50 ml of 6 mol/L phenol-HCl at 110° C. for 24 h and the hydrolysate was filtrated. Then, 2 g hydrolysate was diluted with 3 g of ultra-pure water; 1 g of this solution was combined with a mixture (200 mg) of labeled amino acids ($^{13}C$ and $^{15}N$ amino acids isotope standards, CDN Isotopes, Pointe-Claire, Que., Canada; Cambridge Isotope Laboratories Inc., Andover, Mass., USA) which serves as an internal standard. Samples of the deproteinised plasma and of the hydrolysate were eluted through a poly-prep chromatography column (Resin 100-200 mesh H, BIO RAD, Hercules, Calif., USA) and derivatised with N-(tertbutyldimethylsilyl)-Nmethyltrifluoroacetamide (MTBSTFA) and dimethylformamide (DMF) (Sigma-Aldrich, Ontario, Canada) in a 1:1 ratio. Measurements of [2-15N] Lys and of the amino acids in processed samples were performed using gas chromatography-mass spectrometry (GC-MS, Model CG6890-MS5973, Hewlett Packard Co., Wilmington, Del., USA).

EXAMPLE 2

SBR Setups

Eight 42 L Plexiglas SBRs were used. FIG. 1 is a schematic representation of these digesters. Once loaded, the SBRs consist of a solid, liquid and gas phase. Individual parts are set up on each phase of the SBRs to take samples. The starting sludge volume at the beginning of each cycle was 35 L. All SBRs were operated in a room kept at 25° C. The sludge load for both swine manure and slaughterhouse sludge is 1.5 g COD/L-d. The loading rate of feather keratin was determined according to the limited space of cylinder of AD-SBRs and the total oxygen demand (TCOD) concentration of feathers. The loading rate of feather keratin (adding in bags or adding in mixed liquor) in all SBRs was kept as same (0.21 g COD/L.d). To load sludge into the SBRs, 160 L swine manure or slaughterhouse sludge, was withdrawn from the semi-industrial scale reactors and transferred into a 200 L barrel. A paint mixer was used to keep solids suspended during sludge aliquot. A 5 L container was used to aliquot sludge. Finally, 35 L sludge was transferred into each of the 8 SBRs (4 fed with swine manure and the other 4 with slaughterhouse sludge, respectively.) Before sampling for physiochemical analysis, the reactors were mixed by circulating the biogas for 5-10 min before samples were withdrawn.

All SBR runs and their running conditions are shown in Table 3. Two SBR runs have been carried out. In Run 1, 4 SBR reactors were used to examine degradation of chicken feather in AD-SBRs fed with swine manure. In Run 2, another 4 SBR reactors were used to investigate degradation of chicken feather in AD-SBRs fed with slaughterhouse sludge. Chicken feathers were added in two ways. As shown in Table 3, feather samples were kept in bags in Run 1 and directly mixed with slaughterhouse sludge in Run 2. Feather bags were incubated with distill water in a sealed bucket (6 bags in each) at 25° C. as a negative control.

TABLE 3

AD-SBR running conditions

| SBR run | SBR reactor label | Specification | Sludge source | Feather adding mode | Feather protein load (g COD/L-d) |
|---|---|---|---|---|---|
| 1 | 13 | Control 1 (−feather) | Swine manure | In bags | 0 |
|  | 14 | Control 2 (−feather) | Swine manure | In bags | 0 |
|  | 34 | Positive 1 (+feather) | Swine manure | In bags | 0.21 (in 12 bags) |
|  | 35 | Positive 2 (+feather) | Swine manure | In bags | 0.21 (in 12 bags) |
| 2 | 13A | Control 1 (−feather) | Slaughterhouse sludge | Mixed in sludge | 0 |
|  | 13B | Control 2 (−feather) | Slaughterhouse sludge | Mixed in sludge | 0 |
|  | 15 | Positive 1 (+feather) | Slaughterhouse sludge | Mixed in sludge | 0.21 |
|  | 16 | Positive 2 (+feather) | Slaughterhouse sludge | Mixed in sludge | 0.21 |

EXAMPLE 3

Physiochemical and Microbiological Characterization

All physiochemical factors measured for the AD-SBRs and their sampling frequencies are listed in Table 4.

TABLE 4

Physiochemical factors monitored

| Factors analyzed | Sampling frequency |
|---|---|
| In mixed liquor: TS (total solids), VS (volatile solids), VSS (volatile suspended solids), nitrogen including $NH_3$—N and TKN (total nitrogen), pH & alkalinity, TCOD (total chemical oxygen demand), SCOD (soluble chemical oxygen demand), VFA (volatile fatty acids). | Once a week (Monday) and end of the treatment cycle (Thursday) |
| In bags contain chicken feather: Weight, TCOD, TKN, $NH_3$—N, TS, VS, FS, amino acids | Once at the beginning Once a month in further treatment cycle (weight) |
| Biogas: Total volume, composition ($CH_4$, $CO_2$, $H_2S$) | Total volume once a day Composition once a Week |

The pH, alkalinity, total solids (TS), volatile solids (VS) and volatile suspended solids (VSS) were determined according to standard methods (APHA, 1992, supra). The value of pH was measured using a pH meter. Alkalinity was measured with titration to pH 4.38. TS content was determined by drying a 10 ml sub-sample for 24 h at 105° C. Dried solids were incinerated for 3 h at 550° C. for VS measurement. Similarly, centrifuged slurry was used to determine VSS through incineration for 3 h at 550° C. Soluble chemical oxygen demand (SCOD) was determined by analyzing the supernatant of centrifuged slurry. Total chemical oxygen demand (TCOD) and soluble chemical oxygen demand (SCOD) were determined using the closed reflux colorimetric method (APHA, 1992, supra). Feather bags were taken off and weighed in each month. A new feather bag of the same weight was put in a SBR when a feather bag was taken out. Biogas production was monitored daily using wet tip gas meters and its composition (methane, carbon dioxide, hydrogen sulfide, and nitrogen) was analyzed weekly using a Hach Carle 400 AGC gas chromatograph (Hach, Love-land, Colo.). The column and thermal conductivity detector were operated at 80° C. Total nitrogen (TKN) and ammonia-N were determined using an auto-analyzer according to the macro-Kjeldahl method (APHA, 1992, supra) with a Tecator 1030 Kjeltec auto-analyzer (Tecator A B, Hoganas, Sweden). Volatile fatty acids (VFA) including acetic, propionic, butyric, isobutyric, isovaleric, valeric and caproic acids) were analyzed using an AutoSystem™ gas chromatography equipped with a high resolution megabore column (Perkin-Elmer Corporation; Norwalk, Conn. 06859, USA) connected to a flame ionization detector (Masse et al., 2000, Bioresource Technology, 75: 205-211; Masse et al., 2008, Biorescource Technology, 99: 7307-7311).

EXAMPLE 4

Chicken Feather Keratin (β-Keratin) Biodegradation in Psychrophilic Anaerobic Digestion Sequencing Batch Reactors (PADs) Inoculated with Swine Manure Sludge Freshly plucked white chicken feathers were collected from a slaughterhouse (Principale Street, Saint-Anselme, QC, Canada) and transferred to the laboratory within 4 hours. The chicken feathers were divided into aliquot (2 kg each) parts in clean cotton bags and washed (delicate cycle) in a washing machine (Frigidaire, Martinez, Ga., USA) with tap water. The feather samples were then dried at 45° C. in a Unithern dryer (Construction CQLTD, England) until a constant weight was reached (about eight weeks). The samples were ground in a mill (Thomas-Wiley Laboratory Mill), screened through a 4-mm screen and then divided into aliquot (around 33 g each) parts in nitrogen-free polyester forage bags with a pore size of 50 μm (ANKOM Technology, Macedon, N.Y., USA). The bags were sealed with plastic tie wraps and washed in the washing machine again to remove as much dust as possible. Finally, the washed feather bags were dried at 45° C. until their weights remained constant. When needed, 12 dried feather bags (each containing around 31 g ground feathers) were attached onto a steel stick and inserted into a PAD.

Three 42-L Plexiglas PADs were used in this study. Two of the PADs were inoculated with anaerobic sludge adapted to swine manure. The inocula of the PADs, representing 100% of the volume, came directly from a 7-m³ semi-industrial anaerobic bioreactor that was located at Agriculture and Agri-Food Canada's Dairy and Swine Research and Development Centre (Lennoxville, QC, Canada) and had been treating swine manure at 25° C. over a 2-year period. Twelve feather bags (starting load 4 g/g VS sludge) were added in one of them and the other without adding feather bags was used as a negative control. The third PAD was filled with deionized water containing antibiotics (ampicillin at a final concentration of 100 μg/mL) and added with 12 feather bags to determine the physiochemical loss of feathers from the feather bags. The volume of the inoculum and deionized water for each PAD was 35 L. All PADs were operated in a room kept at 25° C. In run 1, every 30 days, three feather bags were taken out of each PAD, washed with deionized water, dried for 48 h at 45° C., and weighed. Run 2 was start when run 1 was processing in the third month, 12 new feather bags were added into bioreactor and following the same experimental procedure as run 1, the weight deduction of run 2 was also recorded.

TABLE 5

Biodegradation of feather keratin in a PAD seeded with swine manure sludge in run 2

| Day(s) | Weight of feathers (g) | Weight lost (%) |
|---|---|---|
| 0 | 3.1.4 ± 0.1 | 0 |
| 22 | NA | NA |
| 55 | NA | NA |
| 85 | 2 ± 0.6 | 94 |
| 113 | 0.4 ± 0.2 | 98 |
| 150 | 0.14 ± 0.08 | 99 |

Feather keratin degradation in the PAD seeded with swine manure and added with feather bags (feather PAD) was recorded. In Run 1, 86% (from 31±0.3 g at the beginning of the experiment to 5±1.6 g at the end of the experiment) of the feather keratin was degraded after 113 days. In contrast, only a small reduction (<3%) of the feather keratin was observed in the PAD containing water with antibiotics (data not shown). In Run 2, 99% (from 31±0.1 g at the beginning of the experiment to 0.14±0.08 g at the end of the experiment) of the feather keratin was degraded after 150 days (Table 5; FIG. 14). The feather degradation rate in run 2 is higher than in Run 1, indicating that keratin degrading organisms (KDOs) were successfully enriched in Run 1. All result found in this study also demonstrated that the keratinase was an inducible enzyme which can be induced in the presence of keratin. Therefore a proper enrichment process is preferable for efficient degradation of keratin in PADs.

EXAMPLE 5

Bovine Biodegradation in Psychrophilic Anaerobic Digestion Sequencing Batch Reactors (PADs)

Bovine Hooves Preparation

Bovine hooves (α-keratin) were collected from a local slaughterhouse (Colbex, Levinoff, Quebec) that processes about 1000 cattle per day and transferred to the laboratory within 4 hours. The bovine hooves were then washed with deionized water and dried at 45° C. in a Unithern dryer (Construction CQLTD, England) until a constant weight was reached (about one week). Subsequently, the bovine hooves were manually cut into pieces of 3-5 cm in diameter with a drill and ground in a mill (Thosmas-Wiley, Laboratory Mill) through a 2-mm screen. The samples obtained were further ground in a blender (Vita-Mix5200, Vitamix Corporation) and went through a sieve with a pore size of 500 μm. After that, 27 g homogenized bovine hooves were aliquot into nitrogen-free polyester forage bags with a pore size of 50 microns (ANKOM Technology, 2052 O'Neil Road Macedon, N.Y. 14502, USA), sealed with plastic tie wraps; and washed in a washing machine (Frigidaire, Martinez, Ga., USA) using delicate cycle to remove as much dusts as possible. The washed hoof bags were dried again at 45° C. until their weights kept constant. Finally, 12 hoof bags (ca: 27 g each) were attached into a steel stick and put into the bioreactors.

PAD Set Up

Three 42-L Plexiglas PADs were used in this study. Two PADs were inoculated with anaerobic sludge adapted to swine manure. The inocula of the PADs, representing 100% of the volume, came directly from a 7-m³ semi-industrial anaerobic bioreactor that was located at Agriculture and Agri-Food Canada's Dairy and Swine Research and Development Centre (Lennoxville, QC, Canada) and had been treating swine manure at 25° C. over a 2-year period. Twelve hoof bags were added in one of them and the other without adding hoof bags was used as a negative control. The third PAD was filled with deionized water containing antibiotics (ampicillin at a final concentration of 100 µg/mL) and added with 12 hoof bags to determine the physiochemical loss of bovine hooves from the hoof bags. The volume of the inoculum for each PAD was 35 L. All PADs were operated in a room kept at 25° C. Every 30 days, three hoof bags were taken out of each PAD, washed with deionized water, dried for 48 h at 45° C., and weighed. The weight deduction was recorded.

Figure 15:
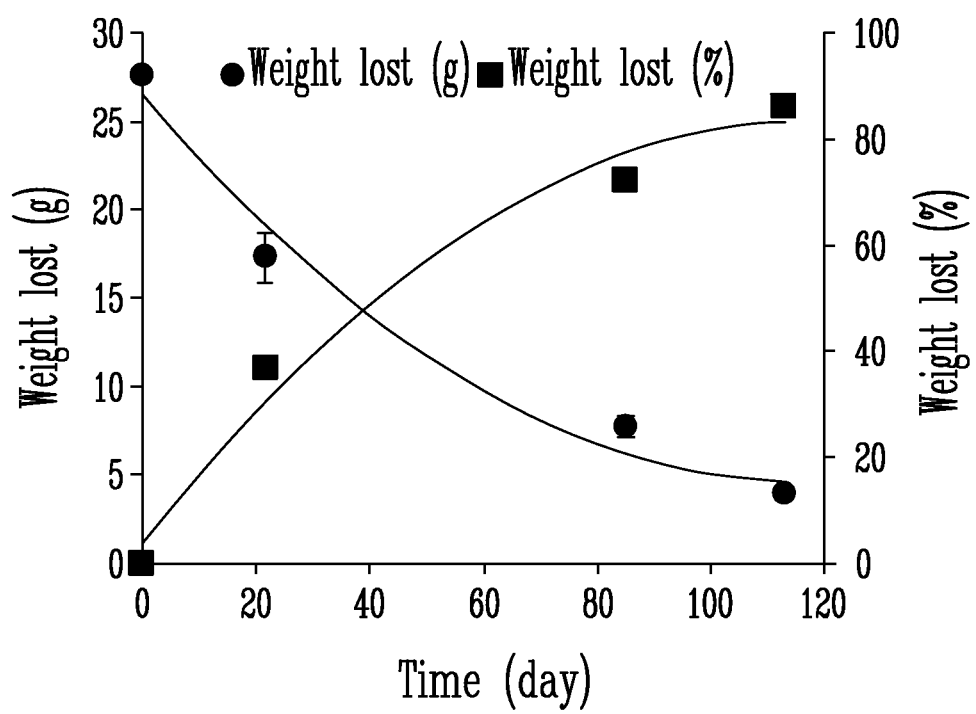
FIG. 15 illustrates the biodegradation of hoof keratin in a PAD seeded with swine manure.

Bovine hoof keratin degradation in the PAD seeded with swine manure and added with hoof bags was recorded. In all individual nylon bags, 86% (from 27.6±0.1 g at the beginning of the experiment to 3.9±0.2 g at the end of the experiment) of the hoof keratin was degraded after 113 days (Table 6; FIG. 15). In contrast, only a small reduction (<10%) of the hoof keratin was observed in the PAD containing water with antibiotics.

TABLE 6

Biodegradation of bovine hoof keratin in a PAD seeded with swine manure

| Day(s) | Weight of bovine hooves (g) | Weight lost (%) |
| --- | --- | --- |
| 0 | 27.6 ± 0.1 | 0 |
| 22 | 17.3 ± 1.4 | 37 |
| 55 | NA | NA |
| 85 | 7.7 ± 0.6 | 72 |
| 113 | 3.9 ± 0.2 | 86 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A process of measuring the efficacy of a sequencing batch reactor to degrade prion proteins in a specified risk material comprising the steps of:
    feeding the specified risk material (SRM) to the sequencing batch reactor (SBR) containing a layer of acclimatized anaerobic sludge;
    adding a model protein to the SBR, wherein the model protein is at least one of perchloric acid-soluble protein, collagen, elastin, and keratin;
    allowing the specified risk material and the model protein to react with the sludge at a temperature of 5° C. to 25° C.; and
    measuring degradation of the model protein to indicate the efficiency of the SBR to degrade prion proteins in the SRM.

2. The process of claim 1, wherein the keratin is β-keratin or α-keratin.

3. The process of claim 1, wherein the keratin is from feather keratin or hoof keratin.

4. The process of claim 3, wherein the feather keratin is from chicken feather.

5. The process of claim 3, wherein the hoof keratin is from bovine hoof.

* * * * *

UNITED STATES PATENT AND TRADEMARK OFFICE
CERTIFICATE OF CORRECTION

PATENT NO. : 8,486,688 B2
APPLICATION NO. : 12/817532
DATED : July 16, 2013
INVENTOR(S) : Daniel Y. Masse and Yun Xia Page 1 of 1

It is certified that error appears in the above-identified patent and that said Letters Patent is hereby corrected as shown below:

On the Title Page

At Item (73) Assignee, before "Bio-Terre Systems Inc. (CA)" insert -- Her Majesty The Queen In Right Of Canada, As Represented by The Minister Of Agriculture And Agrifood (CA) --.

Signed and Sealed this
Twenty-fourth Day of June, 2014

Michelle K. Lee
*Deputy Director of the United States Patent and Trademark Office*